United States Patent [19]
Coppleson et al.

[11] Patent Number: 5,800,350
[45] Date of Patent: Sep. 1, 1998

[54] APPARATUS FOR TISSUE TYPE RECOGNITION

[75] Inventors: John Victor Malcom Coppleson, Potts Point; Bevan Leslie Reid, Weral; Victor Nickaelovich Skladnev, Bondi Junction, all of Australia

[73] Assignee: Polartechnics, Limited, Sydney, Australia

[21] Appl. No.: 799,970

[22] Filed: Feb. 14, 1997

Related U.S. Application Data

[63] Continuation of Ser. No. 332,830, Oct. 31, 1994, abandoned.

[30] Foreign Application Priority Data

Nov. 1, 1993 [AU] Australia ............... PM12137

[51] Int. Cl.$^6$ ..................... A61B 5/00
[52] U.S. Cl. ............. 600/372; 600/373; 600/382; 600/386; 600/407; 600/437; 600/475; 600/477; 600/547
[58] Field of Search ............. 600/547, 437, 600/407, 372–374, 382, 386, 389, 473, 475, 476, 477, 310, 342

[56] References Cited

U.S. PATENT DOCUMENTS

| | | | |
|---|---|---|---|
| 4,213,462 | 7/1980 | Sato . | |
| 4,407,300 | 10/1983 | Davis | 128/734 |
| 4,537,203 | 8/1985 | Machida | 128/734 |
| 4,545,387 | 10/1985 | Balique | 128/664 |
| 4,729,385 | 3/1988 | Juncosa et al. | 128/734 |
| 4,930,516 | 6/1990 | Alfano et al. | 128/665 |
| 4,955,383 | 9/1990 | Faupel | 128/653 |
| 5,036,853 | 8/1991 | Jeffcoat et al. . | |
| 5,042,494 | 8/1991 | Alfano | 128/665 |
| 5,057,695 | 10/1991 | Hirao et al. | 250/575 |
| 5,106,387 | 4/1992 | Kittrell et al. | 606/15 |
| 5,115,137 | 5/1992 | Anderson-Engels et al. . | |

(List continued on next page.)

FOREIGN PATENT DOCUMENTS

| | | |
|---|---|---|
| WO9207513 | 5/1992 | Australia . |
| PM2137 | 11/1993 | Australia . |
| 2486386 | 1/1982 | France . |
| 2126717 | 3/1984 | United Kingdom . |
| 9101687 | 2/1991 | WIPO . |
| 9214399 | 9/1992 | WIPO . |

OTHER PUBLICATIONS

M. Coppleson, et al., "An electronic approach to the detection of pre-cancer and cancer of the uterine cervix: a preliminary evaluation of Polarprobe," *Int'l Gynecol Cancer* 1994, 4, 79–83.

I. Bigio, et al., "The Optical Biopsy System," *Chemical and Laser Sciences Division, Los Alamos National Laboratory*, information document, Mar. 1992.

(List continued on next page.)

*Primary Examiner*—Ruth S. Smith
*Attorney, Agent, or Firm*—Gottlieb, Rackman & Reisman, P.C.

[57] ABSTRACT

A method and apparatus (21, 150) is disclosed for identifying tissue which is suspected of being physiologically changed as a result of pre-cancerous or cancerous activity. The apparatus (21, 150) includes a probe (1, 10; 151) configured to contact the tissue and which includes an arrangement (3–7, 17–47; 158–163) to subject the tissue to a plurality of different stimuli such as electrical, light, heat, sound, magnetic and to detect plural physical responses to the stimuli. The probe (1, 10; 151) connects to an analogue section (23; 152) which buffers signals between the probe (1, 10; 151) and a processor (22; 153). The processor (22; 153) processes the responses in combination in order to categorise the tissue, and then compares the categorisation with a catalogue of expected tissue to identify the tissue, the processing occurring in real-time with an indication of the tissue type (eg. normal, pre-cancerous/cancerous, or unknown) being provided to an operator of the apparatus.

39 Claims, 11 Drawing Sheets

U.S. PATENT DOCUMENTS

| | | | |
|---|---|---|---|
| 5,122,974 | 6/1992 | Chance | 364/550 |
| 5,127,405 | 7/1992 | Alcala et al. | 128/633 |
| 5,131,398 | 7/1992 | Alfano et al. | 128/665 |
| 5,143,066 | 9/1992 | Komives et al. | 128/634 |
| 5,143,079 | 9/1992 | Frei et al. | 128/734 |
| 5,179,938 | 1/1993 | Lonky et al. | 128/18 |
| 5,184,620 | 2/1993 | Cudahy et al. | 600/389 |
| 5,197,470 | 3/1993 | Helfer et al. | 128/634 |
| 5,208,788 | 5/1993 | Dancer et al. | 367/147 |
| 5,247,932 | 9/1993 | Chung et al. | 128/633 |
| 5,261,410 | 11/1993 | Alfano et al. | 128/664 |
| 5,303,026 | 4/1994 | Strobl et al. | |
| 5,304,173 | 4/1994 | Kittrell et al. | 606/15 |
| 5,305,748 | 4/1994 | Wilk | 128/653.1 |
| 5,318,624 | 6/1994 | Kittrell et al. | 128/634 |
| 5,320,101 | 6/1994 | Faupel et al. | 128/653.1 |
| 5,348,018 | 9/1994 | Alfano et al. | 128/665 |
| 5,353,791 | 10/1994 | Tamura et al. | 128/633 |
| 5,353,802 | 10/1994 | Ollmar | |
| 5,369,496 | 11/1994 | Alfano et al. | 356/448 |
| 5,377,673 | 1/1995 | Van Dell et al. | 128/633 |
| 5,377,676 | 1/1995 | Vari et al. | 128/634 |
| 5,386,827 | 2/1995 | Chance et al. | 128/633 |
| 5,398,685 | 3/1995 | Wilk et al. | 128/653.1 |
| 5,402,782 | 4/1995 | Lodder | 128/653.1 |
| 5,413,108 | 5/1995 | Alfano | 128/665 |
| 5,419,312 | 5/1995 | Arenberg et al. | 128/6 |
| 5,427,098 | 6/1995 | Faupel et al. | 128/653.1 |
| 5,439,000 | 8/1995 | Gunderson et al. | 128/634 |
| 5,458,142 | 10/1995 | Farmer et al. | 128/653.1 |
| 5,596,992 | 1/1997 | Haaland et al. | 128/664 |
| 5,598,848 | 2/1997 | Swanson et al. | 600/547 |

OTHER PUBLICATIONS

Coppelson et al. –(1991) Prototype Cervical Probe, Abstract in Int. J. Gynecol. Obstet. XIII. World Congress of Gynecology and Obstetrics.

Vari –(Date unknown) Abstract. Light and laser induced fluorescence spectroscopy (LIFS) and their biomedical applications.

Bornhop –(Date unknown) Abstract. Spectroscopic imaging of tissues using micro–endoscopy.

Wagnieres –(1995) Endoscopic frequency domain florescence lifetime Imaging for clinical cancer photodetection: apparatus design. Proc. SPIE, 2392, pp. 42–54.

Wagnieres –(1990) Photodetection of early cancer by laser induced fluorescence of tumor–selective dye: apparatus design and realization. SPIE vol. 1203 Photodynamic Therapy Mechanisms II, pp. 43–52.

Yoo –(1990) Angle and time resolved studies of backscattering of light from biological tissues. SPIE vol. 1202, Laser–Tissue Interaction, pp. 260–271.

Nabiev –(1994) Applications of Raman and surface–enhanced Raman scattering spectrocopy in medicine. Jour. of RAman Spectroscopy, 25, pp. 13–23.

Nguyen –(1983) Some new color features and their application to cervical cell classification. Pattern Recognition vol. 16, pp. 401–411.

Marino et al. –(Undated) Abstract. On the relationship between surface electrical potentials and cancer.

Avis –(1995+) In–vitro multifrequency electrical impedance measurements and modelling of the cervix in late pregnancy, physiological movement preprint.

Jossinet –(1988) A hardware design for imaging the electrical impedance of the breast. 9 Cain. Phys. Phsiol. Meas., Suppl. A, pp. 25–28.

Macdonald –(Undated) Fundamentals of impedance spectroscopy.

Kelsall –(1987) The open circuit potential decay (OCPD) technique.

Raistrick –(Undated) Theory. The electrical analogs of physical and chemical processes. Physical and electrochemical models.

Geddes –Electrodes and the measurement of bioelectric events. Wiley–Interscience, pub.

Mayer –(1992) Electrode recovery potential. Annals of Biomed. Eng., 20, pp. 385–394.

Foster –(1989) Dielectric properties of tissues and biological materials: A critical review. Crit. Rev. in Biomed. Eng., 17, pp. 25–104, esp. pp. 67–70.

Barsamian –(1985) Origin of dielectric discreteness during the development of Dacus tryoni and its reversal by carcinogen. IRCS Med. Sci., 13, pp. 1103–1104.

Singh –(1979) In vivo dielectric spectrometer. Med & Biol. ENg. & Comput., 17, pp. 45–60.

Record et al. –1994 Bio–impedance active electrode for in vivo measurement.

Eggins –(1993) Skin contact electrodes for medical applications. Analyst 118, pp. 439–442.

Neuman –(1991) Biopotential electrodes, in Medical Instrumentation 2nd Ed., Webster, Ed., pp. 227–287.

Thornton –(1991) Relaxation distribution function of intracellular dielectric zones as an indicator tumorous transition of living cells. IMA Jour. of Math. Applied in Med. & Bio. 8, pp. 95–106.

Panescu –(1994) A nonlinear finite element model of the electrode–electrolyte–skin system. IEEE Trans. on Biomed. Eng., 41, No. 7, pp. 681–687.

McAdams –(1994) The detection of the onset of electrode––electrolyte interface impedance nonlinearity: A theoretical study. IEEE Trans. on Biomed. Eng., 41, No. 5, pp. 498–500.

Boyd –(1989) Modelling the implications for hospital services of cervical cytology screening: A case history.

Ricard –(1990) Detection per operatoire du I–125 et du 1–131 au moyen d'unte sonde portable. J. Med. Nucl. Biophy., 14, No. 2, pp. 151–154.

Narayanswamy –(Undated) Morphological feature detection for cervical cancer screening. SPIE vol. 2424, pp. 265–275.

Nishimura –(1992) Architectural distortion of subcutaneous fascial layer in breast tumors: ultrasonographic evaluation. Ultrasound in Med. & Biol., 18, pp. 815–820.

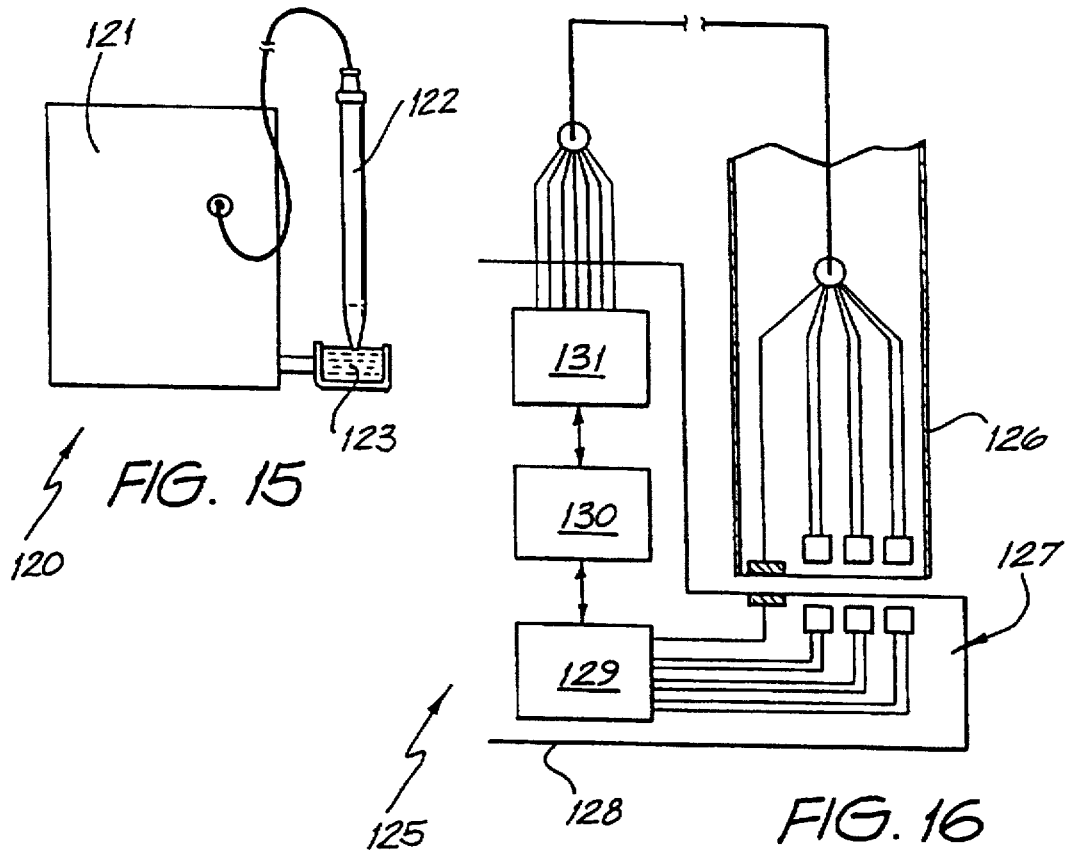
FIG. 15
FIG. 16
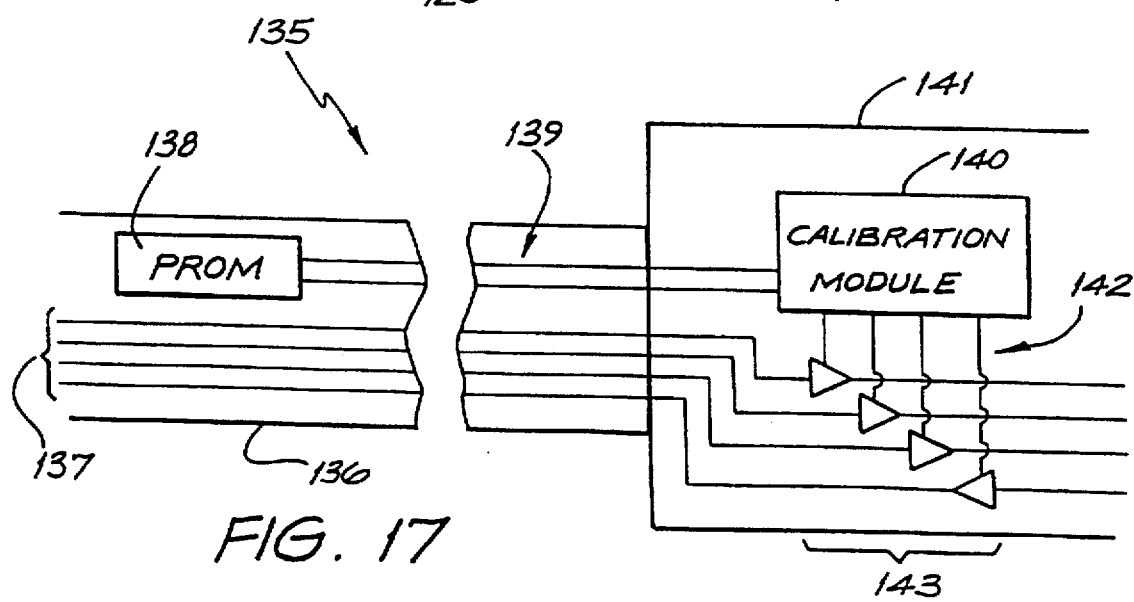
FIG. 17

APPARATUS FOR TISSUE TYPE RECOGNITION

This application is a continuation of application Ser. No. 08/332,830, filed Oct. 31, 1994, now abandoned.

FIELD OF THE INVENTION

The present invention relates to a method and apparatus for identifying different tissue types including those displaying modifications involving pre-cancerous or cancerous stages, diseased tissues, and those that are in a transitional stage.

The identification of different tissue types is provided via a set of measurements of the tissue's physical properties. The present invention relates particularly to the identification of different types of tissues, including external skin and those that can be inspected by means, such as an endoscope, that enable direct access inside the body. A specific application of the invention relates to the inspection of the cervix.

BACKGROUND ART

The early detection of tissues displaying pre-cancer or cancer modifications is important for successful medical treatment. Presently-used detection techniques suffer from inaccuracy and are subject to operator error as well as being time-consuming. A good example of this is the Pap smear for cervical cancer. X-ray diagnosis, which can also be used for detecting advanced cancer modifications, can lead to detrimental exposure to radiation.

A positive result produced by a Pap smear test is generally followed by a visual examination using a colposcope which provides a magnified view of the cervix. Suspect regions of the cervix are evaluated by a skilled practitioner who then makes a subjective judgement of the tissue observed. There are many tissue types in the cervix, some of which display analogous appearances, including visual and textural characteristics, that make clinical diagnosis very difficult and subject to error.

Similar subjective assessments play a major role in the detection and treatment of other locations of neoplastic pre-activity and activity, for example skin melanoma.

Methods and devices have been developed in an attempt to use measurements of physical characteristics of the tissue for distinguishing cancerous tissue from non-cancerous tissue. Electrical measurements of the skin or tissue have been used. Such electrical measurements on their own do not provide the information needed for an effective diagnosis.

In U.S. Pat. No. 4,537,203 to Machida, an abnormal cell detecting device having a pair of electrodes attached to a portion of the body is disclosed. Two voltages at different frequencies are applied between the pair of electrodes. The capacitance measured at the two frequencies gives an indication of the presence of abnormal cells.

In U.S. Pat. No. 4,955,383 to Faupel, a method and apparatus for determining the presence or absence of a diseased condition in a tissue is disclosed. Skin surface potentials are measured using an electrode array.

In U.S. Pat. No. 5,143,079 to Frei et al, an apparatus for the detection of tumour in tissue is disclosed. The apparatus includes means for determining the dielectric constant of living human tissue. The impedance of a specific area depends on the dielectric constant and the conductivity of the tissue. Inhomogeneities in the tissue give rise to variations of the impedance.

It is also known to measure the physical characteristics of a tissue by optical measurements. For example, a device described in U.S. Pat. No. 5,036,853 by the present applicant is used to identify cervical tissue which is suspected of being physiologically changed as a result of neo-plastic activity or pre-activity of a cervical lesion. In this arrangement, correct positioning of the probe device relative to the surface of the cervix is required to avoid incorrect measurements. The device as described in that patent is unable to ensure correct positioning.

The above mentioned arrangements suffer from a number of disadvantages. In particular, each is generally configured for use with a particular type of cancer which is presented to the physician under generally the same conditions. Accordingly, such devices are not able to be used effectively for a plurality of tissue and cancer types, such as cervical, skin, colon etc, and conveniently at locations at which those cancers are found.

SUMMARY OF THE INVENTION

It is an object of the present invention to provide a method and apparatus for tissue type recognition which permits use at a variety of locations within or about a living being and that can quickly produce an objective identification of the tissue types including the presence of pre-cancerous and cancerous activity.

According to one aspect of the present invention there is disclosed an apparatus for identifying different tissue types including those displaying modifications involving pre-cancerous or cancerous activity, said apparatus comprising a probe having one end shaped to face said tissue and comprising at least two paths for electromagnetic radiation, at least one of said paths leading to said one end arranged to convey said electromagnetic radiation in a first direction towards said one end, and at least one of said paths leading from said one end and arranged to convey said electromagnetic radiation in a second direction away from said one end;

a first electromagnetic generator means connected to said at least one said first direction path to transmit said electromagnetic radiation at a first or associated with a first wavelength along said at least one first direction path and a second electromagnetic generator means connected to said at least one first direction path to transmit said electromagnetic radiation at a second wavelength along said at least one first direction path, said second wavelength being different from said first wavelength;

receiving means connected to said at least one second direction path to receive said radiation at said first and second wavelengths backscattered by said tissue;

at least one electrode means to apply electrical signals to said tissue and electrical measuring means to measure resulting electrical response by said tissue; and comparator means to compare the measured electrical signals and the measured received radiation and compare same with known values to thereby identify the tissue type.

It is to be noted that where the term "wavelength" is used in connection with sources of electromagnetic radiation, the spectral bandwidth of such sources will be finite.

According to another aspect of the present invention there is disclosed a method of identifying tissue which is suspected of being physiologically changed as a result of pre-cancerous or cancerous activity, said method comprising the steps of:

irradiating said tissue with electromagnetic radiation at a first wavelength;

irradiating said tissue with electromagnetic radiation at a second wavelength, said first and second wavelengths being different;

receiving the radiation at said first and second wavelengths backscattered by said tissue;

supplying electrical signals to said tissue and measuring the resulting electrical response of the tissue;

generating mathematical transformations of said received radiation and electrical response signals and identifying the condition of said tissue by comparing said mathematical transformations with a catalogue of the key features of normal and abnormal tissue types.

It is noted that backscattered radiation includes reflected radiation.

In accordance with another aspect of the present invention there is disclosed a method of identifying tissue which is suspected of being physiologically changed as a result of pre-cancerous or cancerous activity, said method comprising the steps of:

(a) subjecting the tissue to a plurality of different stimuli;

(b) detecting a corresponding tissue response to each stimuli;

(c) processing each response in combination to categorise the tissue; and (d) comparing the categorisation of the tissue with a known catalogue of expected tissue types to identify the tissue.

In accordance with another aspect of the present invention there is disclosed apparatus for identifying tissue which is suspected of being physiologically changed as a result of pre-cancerous or cancerous activity, said apparatus comprising:

a plurality of energy sources configured to impinge upon or to contact said tissue and to stimulate same with a plurality of different stimuli, a plurality of detectors configured to detect responses of said tissue to a respective one or plurality of said stimuli and to couple said responses to a controller, said controller including a processor arrangement configured to process said responses in combination in order to categorise said tissue, a memory arrangement comprising a catalogue of expected tissue types, and a comparison arrangement for comparing the categorisation of said tissue with said expected tissue types from said catalogue so as to identify same, and an indicator arrangement for indicating to a user of said apparatus the tissue type identified, or the probability thereof.

BRIEF DESCRIPTION OF THE DRAWINGS

A number of embodiments of the present invention will now be described with reference to the drawings in which:

FIG. 9 illustrates another embodiment of a sensor specifically configured for detection of skin cancers and the like;

FIG. 10 is a perspective, partially cut-away view of a further embodiment of the invention for detection of skin cancers and the like;

FIGS. 15 and 16 show two arrangements for probe calibration;

FIG. 17 shows a further embodiment of probe calibration; and

BEST AND OTHER MODES FOR CARRYING OUT THE INVENTION

Figure 1:
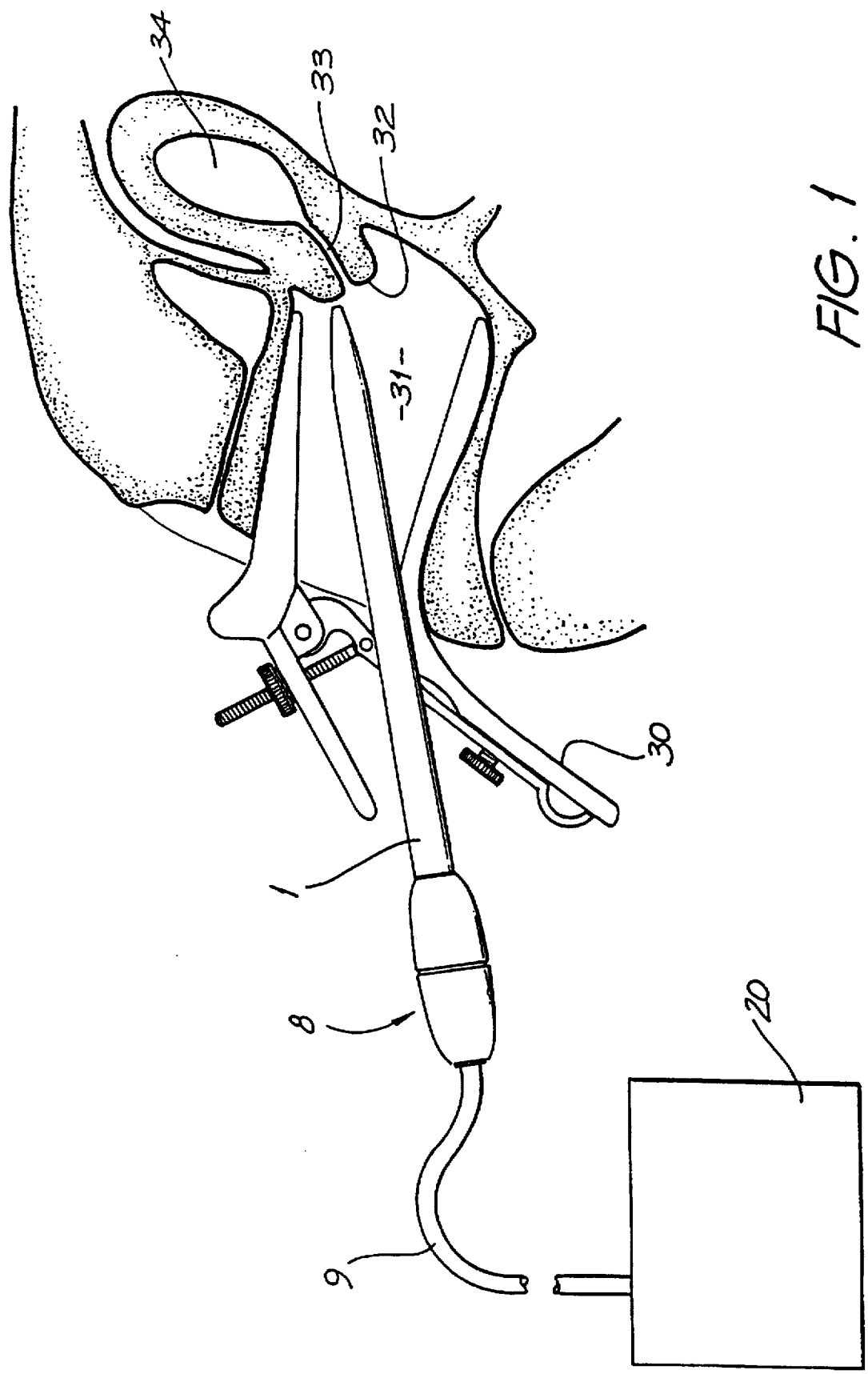
FIG. 1 is an illustration, partially in section, of a probe system of one embodiment in use.

Cancer detection through optical sensing often involves imaging of a tissue region in question onto a sensor array. Such a technique imposes a number of limitations. Firstly, transmission through and scattering of the tissue and its environs are more significant for cancer detection than surface reflection from the tissue. Optical imaging sensors respond primarily to surface reflections. Secondly, the sensed image is usually grossly affected by interfering properties of the tissue surface such as surface reflectivity, emissivity, specular reflection, surface fluids and ambient light. Thirdly, the optical signal received by each pixel of the sensor array is generally decomposed spectrally into only a few wavelength regions as with red, green and blue (RGB) camera systems. Fourthly, it is not feasible to make simultaneous electrical, magnetic or acoustic measurements on each projected pixel of tissue. Such measurements, as the present inventors have found, can be most important, in combination with the optical information to discriminate the tissue type in that region. Also, the subject region is not always sufficiently accessible to be illuminated by and sensed with an imaging system, such as a camera.

When a tissue is viewed with the naked eye or through an imaging system, what is observed in the image is the illuminating light being reflected by each minute region of tissue. This represents primarily, surface reflected light, and can be highly influenced, if not dominated by, fluids prevailing on the surface, oxidising agents or other chemical or pH phenomena existing at the surface, surface temperature, as well as the type and angle of illumination. Light from cells or tissue at or near the surface thus generally has less discriminatory information regarding cancer or pre-cancer, when compared to light from cells or tissue at slightly deeper environs, which are largely visually obscured by surface reflections. Hence a system that accesses optical properties of these deeper cells as a signal whilst excluding reflections from the surface cells, is highly desirable. The means used in the described embodiments to achieve such discrimination is "controlled spatial separation and optical isolation" between the region of tissue irradiated and the region of tissue from which the radiation is examined.

In viewing with the naked eye, or through a conventional optical imaging system, there is no equivalent process for observing the localised transfer properties of each "pixel" of tissue so described. The latter are a consequence of a complex dynamic between transmission, absorption, scattering and retro-reflection whose end effect can produce tissue identification superior to a surface reflection. This process, referred to herein as backscattering, constitutes a basic mechanism employed in the preferred embodiments to be described.

When the information from an ensemble of regions in proximity whose backscattering ability has been measured is reconstructed as an optical image (ie reconstructed in the same spatial order as the measurements were taken), it forms a "image" of backscattered values over the reconstruction surface. Such an image is herein called a "backscattered image" and it can provide a valuable mapping to identify cell and tissue type over a region. One embodiment of the present invention provides a means for creating such backscattered images. In addition, the inclusion of electrical measurement data related to the locally prevailing dielectric and impedance properties of the tissue at each pixel of the image provides a multi-dimensional imaging mechanism. The mechanism of backscattered imaging as described herein includes the concept of measuring any one or more of the electrical, magnetic, acoustic, ultrasonic, thermal, optical, and the like physical parameters at each pixel region, and is particularly relevant to the described embodiments. The backscattered image thus can include a characterisation at each pixel region of a multiplicity of energy types and physical mechanisms.

A backscattered image thus can include a characterization, at each pixel region, of a multiplicity of energy types and physical mechanisms. While backscattered signal variables would primarily be of a stimulate/receive transfer nature, the included measurement of self properties at each pixel region (like prevailing temperature or electrostatic potential), is not herein excluded within the definition of a backscattered image.

Because in cancer detection it is particularly important to asymptote toward achieving zero false negative results, it is often desirable to utilize as many independent discriminators as feasible to distinguish tumorous cell types. For example, if a given mechanism involving an independent stimulate/receive energy form (eg., magnetic) yields only a 1% added statistical contribution toward determination of tumorous cell types, and the summed effect of the other energy forms utilized statistically discriminate to 98% accuracy, (eg. optical and electrical), the compound addition of 1% magnetic contribution can halve the system inaccuracy from [100%−98%]=2% to [100%−99%]=1%, (for optical, electrical and magnetic). Thus the contribution of a seemingly small independent statistical-discrimination-capability can yield significantly improved overall system performance and may well warrant inclusion. For this reason, multiple measurements which involve many different energy forms and mechanisms, (while more cumbersome to implement or difficult to build into one small probe necessitating micro-miniaturization technologies), represent desirable features of the preferred embodiment.

It is therefore desirable to utilise an appropriately configured probe which can provide access to the surface of the tissue and circumvent some or all of the limitations discussed above. In the case of cancer detection near a region where admittance is through a physical probe, it is important to access the tissue surface while allowing substantial visual feedback, and permitting the greatest positioning dexterity for the clinician. Accordingly, embodiments where a probe is used should be configured to maximise visibility with minimum obscuration while at the same time permitting stimulating sensors to follow the contour of the subject tissue. The accuracy with which the tissue type can be established in proximity to the surface is highly dependent upon such functions. Control of orientation to the surface direction, to pressure against the surface, exclusion of unwanted sources of instrumentation noise such as background light, fluids, parasitic electromagnetic or mechanical vibrations are important to achieve precise measurements.

Moreover, these constraints on measurement accuracy interdepend upon the methods employed to bring the stimuli energy to and from the tissue surface regardless of whether the stimuli is electrical, optical, acoustic, magnetic, thermal or ultrasonic.

With an imaging probe of the described embodiments, it is preferred to collectively accumulate data over each spatial region of interrogation so that a decision about the region can be based upon a multiplicity of N readings rather than a single reading. Such a sampling process is likely to result in a statistical improvement in precision proportional to $\sqrt{N}$. It is also convenient to be able to ascertain a resultant "picture" analogous to pictures on a computer screen derivable through an imaging system, of each of the cell or tissue types over the subject region.

Thus, in the design of a pre-cancer and cancer detection system which measures physical variables, it is appropriate to have a data acquisition system accommodating a multiplicity of probe types, each specifically configured to address the application involved. The probes should therefore be interchangeable with automatic calibration when changed. It is also important to provide the clinician administering the test with feedback regarding any misuse, disorientation or inappropriate or prevailing conditions that could invalidate the test in process.

Such information should be readily or immediately available along with other cautionary alarms concerning momentary proximity of the sensing probe to cancerous or pre-cancerous tissue. During use, the clinician is likely to be absorbed in manipulating the probe onto tissue regions of concern, and therefore cannot focus attention onto a computer screen or other conventional display or indicator. Configurations which provide adequate real time feedback to the clinical operator, while at the same time storing essential measurement data, are thus relevant ingredients in a cancer measurement instrument.

Because probes are usually employed in environments containing fluids which have varied optical and electrical properties, it is a further difficulty to calibrate transmission and receive sensors and electrical performance in a manner which copes with this variability. Optical measurements are desirably based on transmission, absorption, backscattering by the body of the material rather than surface reflectance. Placing the probe tip normal to a reflectance standard for calibration will yield a response primarily due to surface reflection reflectance of the standard. In such calibration, the emit/receive ratio would not be monotonic with distance from the reflectance standard to the probe face and it would also be highly dependent upon that distance. It is thus a formidable problem to simulate conditions of actual measurement in this calibration process.

Semi-conductor and other components utilised in a probe which will be handled by an operator and will intermittently contact tissue surfaces and will change in temperature because of the difference between room and tissue temperatures. Particularly for components which comprise semiconductor junctions at the probe face, variability of performance can be a significant consequence of temperature change. It is thus desirable that the data handling system compensate for the instantaneous temperature such components possessed while measurements are being made.

At the present time, underlying mechanisms which create physically measurable distinctions between normal, precancer and cancerous tissue types are only understood in terms of phenomenological models. For an arbitrary type of cancer, one cannot predict the precise significance of each discriminant parameter. As a consequence, the process of calibrating such a cancer detection instrument is directly interlinked with any discrimination algorithm employed and the foundation measurements upon which the algorithm is based. This means that only when stable, repeatable probe designs of appropriate geometry, efficiency and electro-optic (for example) performance are used to collect reliably accurate data regarding cancer and its pre-cancerous states, can a design algorithm be truly optimised. Thus, the means by which the algorithm is optimised through successive iterations becomes part of the calibration process and a means for achieving results obtained by the various embodiments.

One or more electrodes can be used to provide a number of discriminants which can be used in the identification of tissue types. When using a single electrode, the patient is grounded by having some form of contact with another part of the body. For example, an electrode as used in electrocardiograph (ECG) readings, or one hand in a salt solution or a conductive wrist band as used by electronics workers. The use of multiple electrodes enable their relative readings to be additionally used to establish that other measurements, for example optical measurements are well founded through the optical transducers being appropriately seated against the tissue surface. Asymmetry of readings from symmetrically located electrodes indicate asymmetry of the probe tip with respect to the tissue surface.

Electrodes can take the form of metal discs at the face of an insulator achieved by using wires truncated at the face. The electrodes can take any one of a number of shapes and can include circles, ellipses, squares, rectangles, triangles, segments of circles or segments of annuli, and their orientation can be symmetrical or asymmetrical to the centroid of the tissue section being scrutinized.

The electrode surface itself can be metallic or non-metallic. For example, the electrode can comprise a semiconductor such as silicon, carbon or titanium dioxide bonded upon titanium.

Alternatively, the electrode can comprise an electrolytic cell (eg silver/silver chloride, or mercury/calomel) coupled to the tissue by a salt bridge. A salt bridge in the form of an electrolyte containing gel or sponge or porous plug which can be used with a metal electrode also.

Electrodes can be used to measure a number of electrical properties of the tissue, such as:

conductivity, by determining the in-phase current flowing when a sine wave voltage is applied to the electrodes, over a range of frequencies;

the complex impedance of the system over a range of frequencies;

the current flow into the electrodes on the tissue as a voltage is applied. The current flow may be analysed in terms of its temporal or its frequency components (eg. by Fourier analysis). The temporal analysis may be in terms of the shape of the current flow versus time curve, the parameters in the equation of that curve, or the values of components in an equivalent electrical circuit;

the current flow out of the tissue after the cessation of a voltage pulse applied to the electrodes. The analysis may be temporal or frequency related as above; and the voltage decay without drawing current after the step removal of an applied voltage that has been sustained constant for a sufficient time for this system to reach equilibrium prior to its removal (ie. the voltage decay into a very high impedance).

An electronic circuit employed to perform the above measurements can be hard wired or it can be under software control by a computer. In the latter case the type of measurements performed may vary depending upon the results of previous measurements.

This facility is important for the purpose of establishing that the probe is accurately placed on the tissue so that readings, electrical, optical and other, can be expected to be reliable. Data should be rejected automatically if the probe orientation is outside an acceptable range. Various electrode configurations and signal analysis circuits can be chosen to suit the needs of the software. With some types of tissue, the computer may not be able to come to an unambiguous diagnosis using the standard measurement regime. In that case, the circuit can be changed by the software and other, complementary determinations can be made.

The probe should be able to be manipulated either across the surface of the human body or within the human body using a speculum or other assisting instruments that provide the clinician with an unimpeded view of the tissue being probed. There should also be sufficient clearance to allow for a high level of illumination, particularly where optional video recording of the data sampling is being made. In many internal applications, the size of the area that the probe should be able to respond can be as small as 2 mm in diameter. Accordingly, the resolution of the probe must be sufficient to resolve pre-cancerous tissue of that size.

Having set out various preferred criteria that are useful in achieving pre-cancer and cancerous tissue detection, a number of specific embodiments can now be described.

FIG. 1 shows an arrangement for detecting pre-cancerous and cancerous tissue which includes a probe 1 coupled to a controller 20 via a cable 9 connected to the probe 1 via a coupling 8. The probe 1 in this embodiment is being used to detect cervical cancer, and FIG. 1 further illustrates a speculum 30 being used to open the walls of the vagina 31 of a patient, to expose to the tip of the probe 1, the cervix 32 which terminates the birth canal 33 that provides a path into the uterus 34. The probe 1 is moved about the entire surface of the cervix 32 in order to stimulate tissue of the cervix 32 and obtain responses to the stimuli which can be processed by the controller 20.

Figure 2:
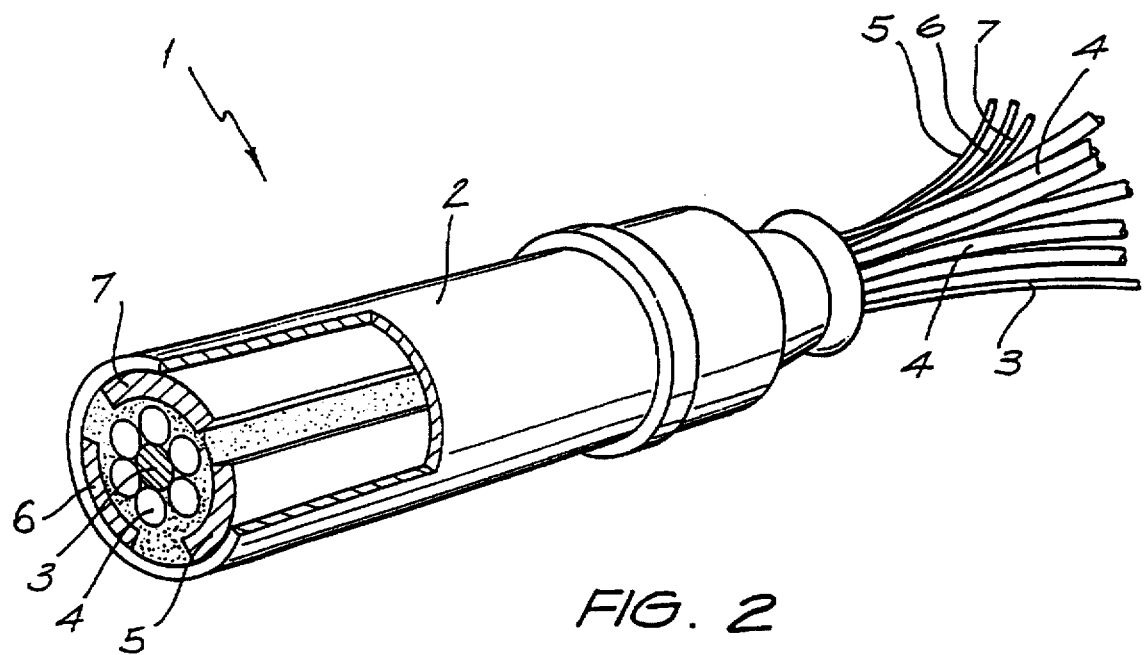
FIG. 2 is a schematic representation of a probe of a first embodiment.

As shown in FIG. 2, probe 1 includes an external tube 2 which provides electrical insulation and mechanical strength. Located within the tube 2 is a first electrode 3 which is in the form of a flat end of an electrical wire which is positioned in the centre of a bundle of optical fibres 4. Three other electrodes 5,6,7 are segments of a cylindric metal tube which are positioned adjacent and abutting against the internal surface of the external tube 2.

Figure 3:
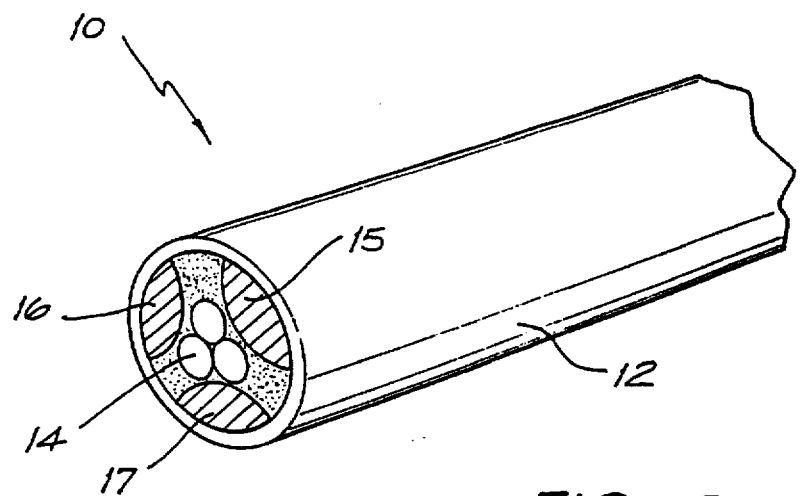
FIG. 3 is a schematic representation of a probe of a second embodiment.

A second embodiment of a probe 10 useful in the arrangement of FIG. 1 is illustrated in FIG. 3. This embodiment of the probe 10 presents a more compact design which is realised using only three electrodes 15,16,17 having a different shape to the electrodes 5,6,7. The shape of the electrodes 15,16,17 ensures that the electrical and optical measurements are made on the same area of tissue. The electrodes 15,16,17 are adjacent to and abut against an external tube 12, with a bundle of three optical fibres 14 positioned therebetween.

Using the probe 1 of the first embodiment, three initial electrical measurements are made between the central first electrode 3 and each of the other electrodes 5,6,7. The results of these measurements are compared and if the results differ significantly, the measurements are discarded because it indicates that the tip of the probe 1 is not in uniform contact with the tissue.

In the preferred embodiment pulse measurements are used both for optical and electrical properties, as a method to reduce noise and mutual interference between the measured signals. For this reason, an example of the invention as described in reference to FIGS. 4 and 5 includes the use of a sequence of electrical pulses.

Figure 4:
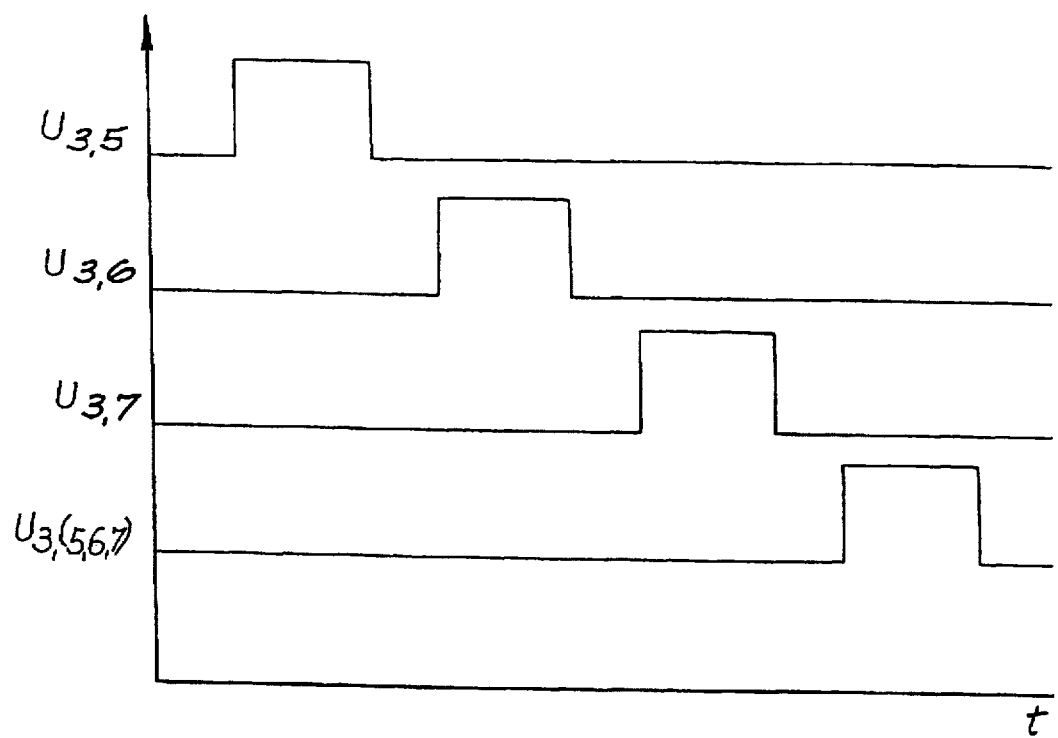
FIG. 4 is a graph of a sequence of electrical pulses used for the embodiment shown in FIG. 2.

In FIG. 4, a graph of a sequence of electrical pulses is illustrated for the use of the probe 1 of FIG. 2. A voltage pulse $U_{3,5}$ is applied between the electrodes 3 and 5 with electrodes 6 and 7 disconnected. This pulse is followed by a pulse $U_{3,6}$ between electrodes 3 and 6 with electrodes 5 and 7 disconnected. This is followed by a pulse $U_{3,7}$ between electrodes 3 and 7 with electrodes 5 and 6 disconnected. During and immediately after each pulse $U_{3,5}$, $U_{3,6}$ and $U_{3,7}$, the system measures the electrical responses which are then stored and compared. This will be described below. If the results differ significantly the results are discarded because it indicates that the tip of the probe 1 is not in uniform contact with the tissue. To enable a large number of readings to be taken, the pulse duration and the sequence duration are relatively short, typically in the tens to hundreds of microsecond region to provide real-time useful information. If the measurements indicate a correct positioning of the probe 1, then a fourth measurement is performed with a symmetric connection of the electrodes, ie., a voltage pulse $U_{3(5,6,7)}$ is applied between electrode 3 and electrodes 5,6,7.

Figure 5:
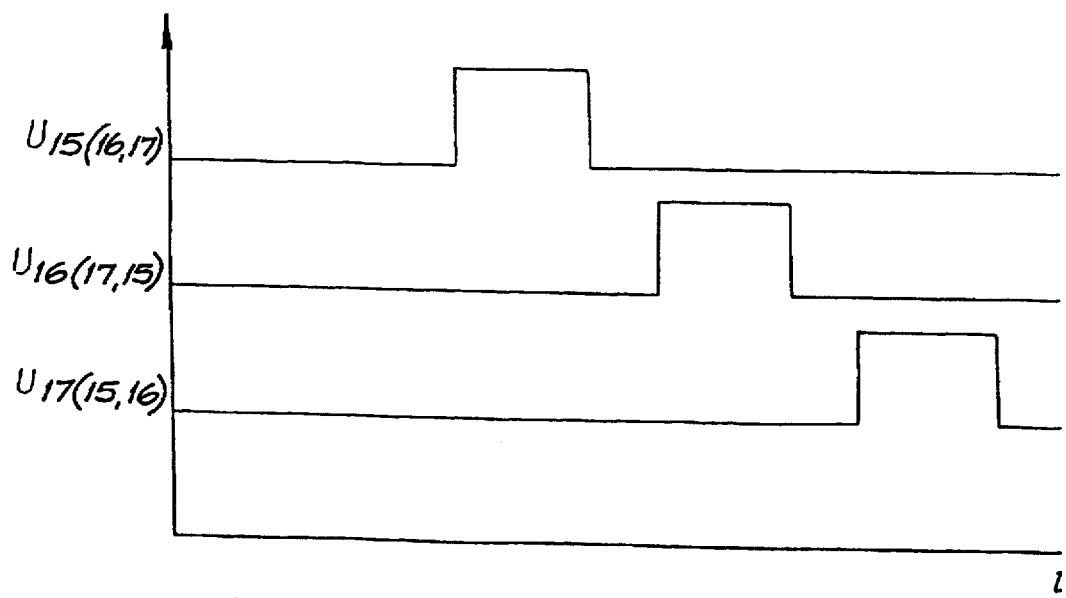
FIG. 5 is a graph of a sequence of electrical pulses used for the embodiment shown in FIG. 3.

FIG. 5 illustrates a similar sequence of electrical pulses used for the configuration shown in FIG. 3. In this embodiment, the symmetry of the electric field at a given time is no longer realised. Three electrical pulses, $U_{15(16,17)}$ applied between electrode 15 and connected electrodes 16 and 17, $U_{16(17,15)}$ applied between electrode 16 and connected electrodes 17 and 15, and $U_{17(15,16)}$ applied between electrode 17 and connected electrodes 15 and 16, are used. The relative magnitudes of the measured responses indicate a correct or incorrect positioning of the probe, to provide an indication of operator error.

In another form of the invention, it is possible to use only one electrode in the probe, the second connection to the skin or tissue can be made using any one of a number of convenient methods, eg., a conductive pad to some part of the body.

Using the probes 1 and 10 of the above embodiments, the electrical properties of the tissue can be determined in a number of ways. For example, a rectangular electric pulse can be applied to the electrodes as described above, and the time varying current that flows into and out of the tissue can be measured either as a current in the circuit, or as a time variant potential difference between the electrodes subsequent to the pulse. The shape of these time variant signals is a measure of the electrical properties of the tissue. Alternatively, electrical signals of various frequencies can be used to measure the tissue electrical characteristics. The magnitude of the voltage applied to the tissue during the measurements needs to be large enough to ensure that the signals being measured are above any ambient noise signals that may be present but in general should not exceed two volts so as to avoid discomfort to the patient.

The optical properties of the tissue can be measured over a range of wavelengths from ultraviolet to far infra-red. One of the optical fibres in the probes 1 and 10 is used to guide electromagnetic radiation from one or more sources to the surface of the tissue where it is absorbed and scattered. A second fibre which can be adjacent to or a short distance away from the first fibre guides the radiation from the tissue back to one or more detectors (not illustrated). The magnitude of signals from the detectors provide a measure of the optical properties of the tissue.

The sources of the electromagnetic radiation can conveniently be light emitting diodes (not illustrated) or solid state lasers (not illustrated). Several wavelengths can be guided down one fibre 4,14, or separate fibres 4,14 can be used for each wavelength. Amongst the wavelengths that have been found to be highly diagnostic are 540, 650, 660, 940 and 1300 nm.

Figure 6:
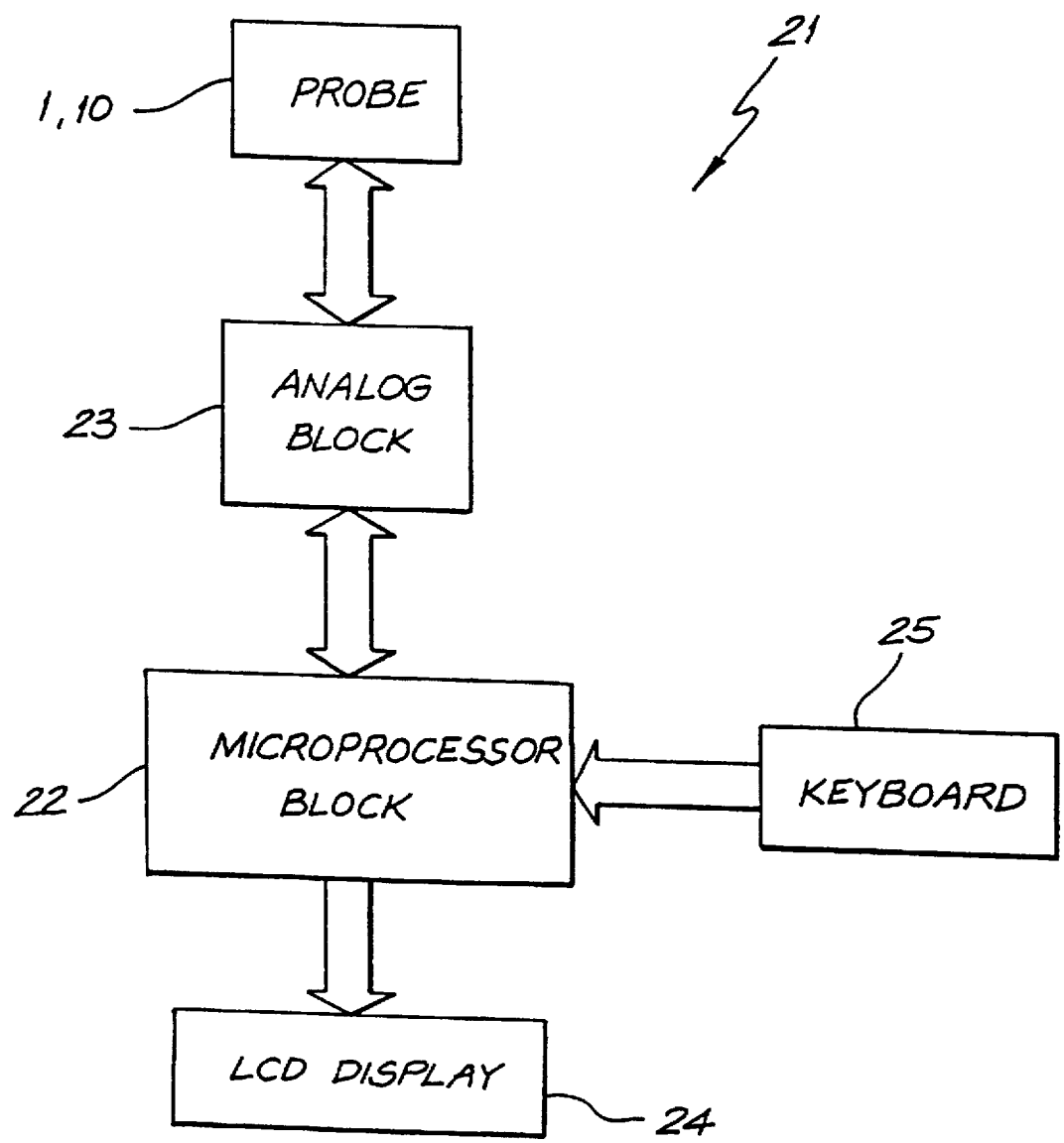
FIG. 6 is a schematic block diagram representation of a detection system of one embodiment.

The controller 20 includes a dedicated computer system 21 as illustrated in FIG. 6 that can supervise the apparatus of the preferred embodiment. The system 21 includes a microprocessor block 22 which controls, via an analog block 23, adequate synchronisation for the electrical signals applied to the electrodes 3,5,6,7,15,16,17 of the probes 1 and 10 respectively and the optical emitters (not illustrated). The signals from electrical and optical detectors are processed in the microprocessor block 22 and the results can be shown on a display 24 or can cause activation of other visible, audible, or printing indicators. A keyboard 25 is able to be used by an operator to provide commands to the computer system 21.

Figure 7:
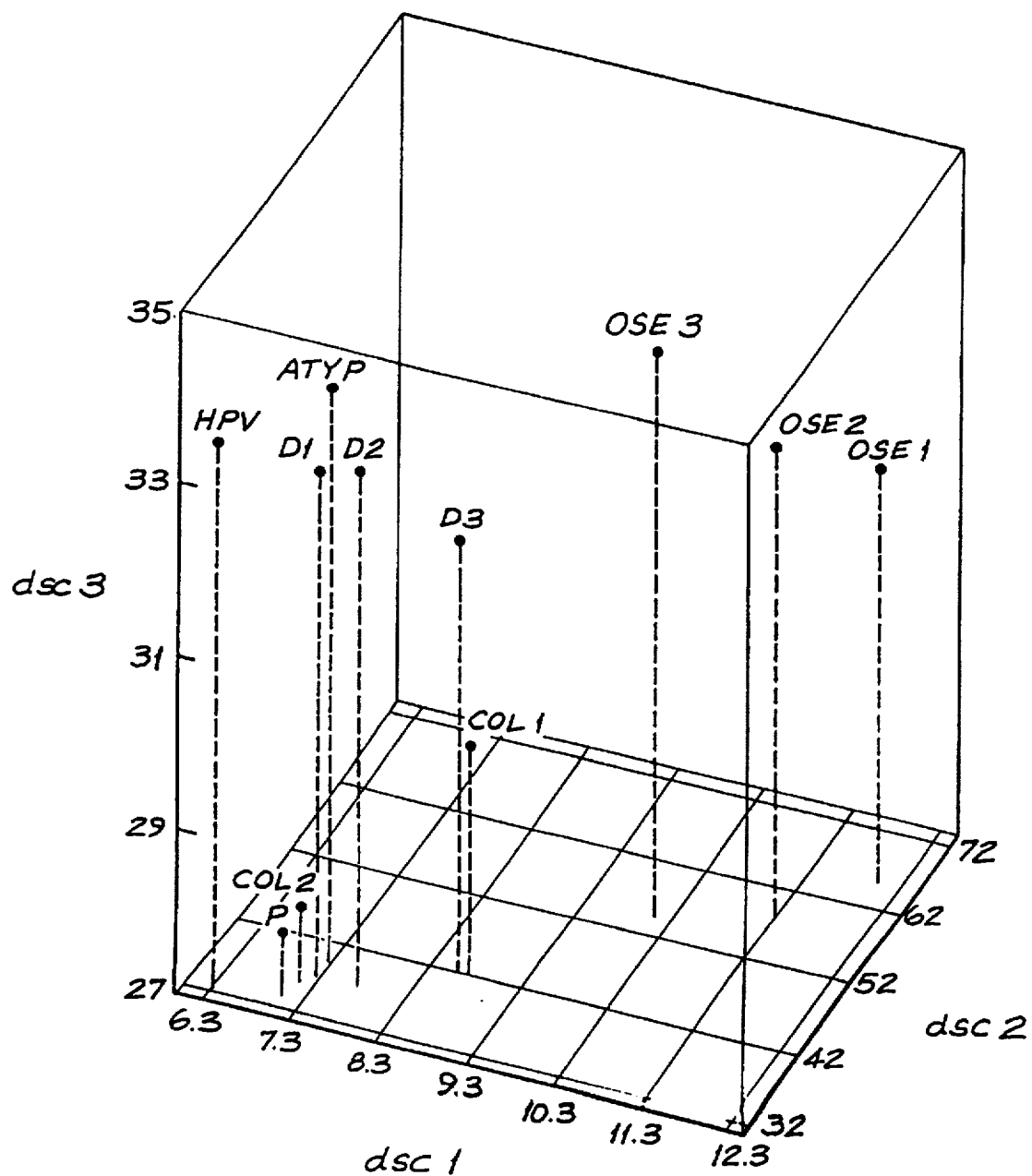
FIG. 7 is an example of a graph showing a group of tissue types as a function of three discriminants obtainable from electrical and optical measurements.

The data which has been collected by the computer system 21 is processed and compared with data that has been stored in the memory of the computer system 21 in the form of patterns of data specific for each tissue type. FIG. 7 illustrates a typical graph of tissue types as a function of three discriminants obtainable from electrical and optical measurements.

The three discriminants employed in the preparation of FIG. 7 were two measures of backscattered light (dsc1, dsc2—each at a corresponding wavelength) and a measure of the shape of the electrical relaxation curve derived by Fourier analysis (dsc3). FIG. 7 demonstrates how the normal tissue types Original Squamous Epilethium (OSE1, OSE2, OSE3), Columnar (COL1, COL2) and Immature metaplasia (P) are distinguished from the abnormal, pre-cancerous tissue types Human Papilloma Virus (HPV), Atypia (ATYP) and Precancer (D1, D2, D3).

The results of this comparison are communicated to the operator via the display 24 or other appropriate means. The results can be stored in the microprocessor block 22 for particular patients and later retrieved or printed out.

In the embodiment of FIGS. 1 to 7, probes 1 and 10 of an elongated straight outer tube where appropriate, a flexible shaft can be provided or the probe incorporated in a capsule whereby insertion using a catheter arrangement can be achieved.

Figure 8:
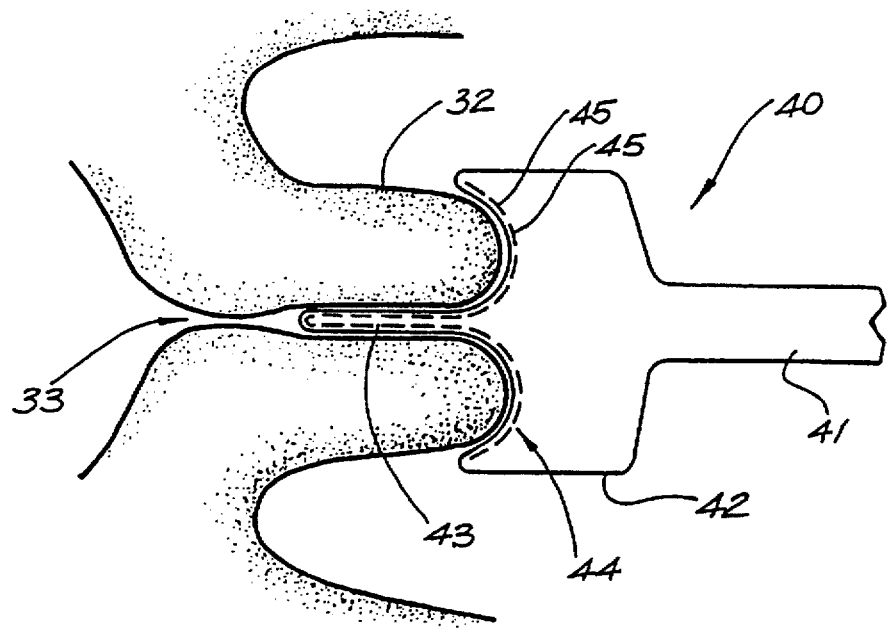
FIG. 8 illustrates the use of an embodiment of a probe specifically configured for detection of cervical pre-cancers.

FIG. 8 illustrates a probe 40 specifically configured and shaped to sample tissue types on the cervix 32 of a patient. In particular, the cervical probe 40 includes an elongate shaft 41 which can be held by the clinician and which interconnects to a cable (not illustrated) which supplies to the control unit. The shaft 41 terminates in a main body 42 from which a central probe portion 43 extends, into the birth canal 33, and which is surrounded by an annular depression 44 configured to cup the cervix 32 therewithin. The probe portion 43 and the depression 44 have distributed across their surfaces repeated arrays of stimulate/receive elements 45 which are configured to sample physical properties of the tissue along the entire contour of the cervix 32. The sensors 45 interconnect to the controller via the shaft 41. Because a multiplicity of stimulate/receive energy types can be applied at a plurality of contiguous regions along the entire contour of the probe face, a composite backscattering picture can be ascertained with a single twist of the shaft 41 by an operator.

Figure 9:
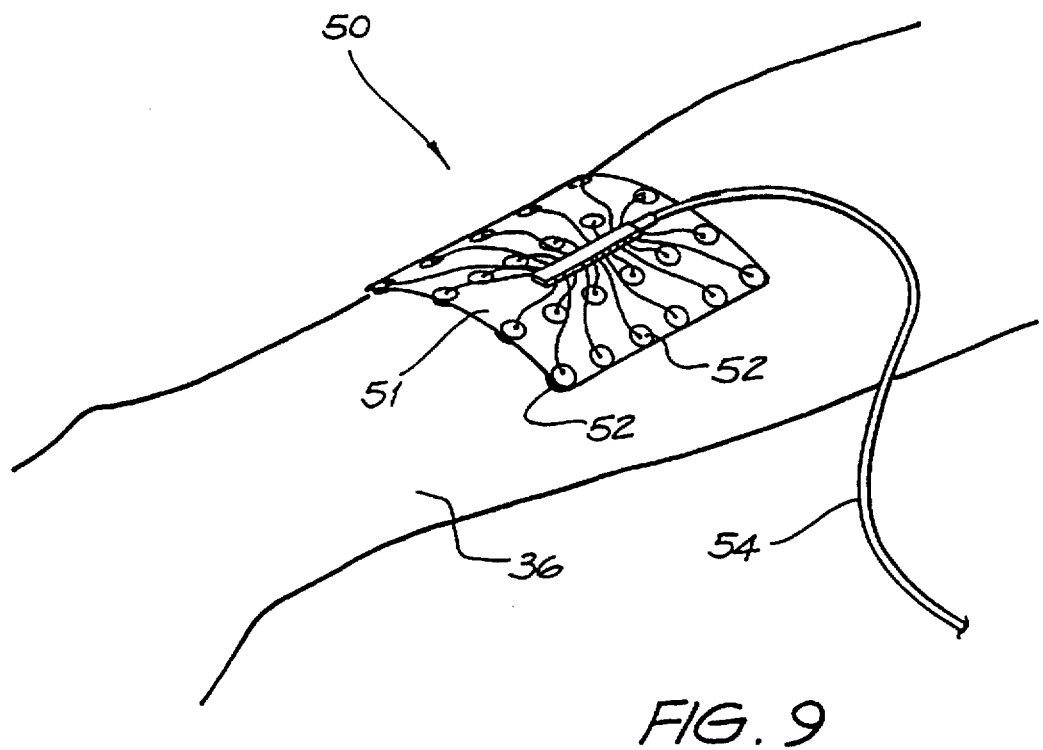

In FIG. 9, a flexible probe 50 is shown which is configured to be applied specifically to skin, in this case, upon the arm 36 of a patient. The probe 50 includes a flexible printed circuit planar substrate 51 upon which a number of sensors 52 are configured. The sensors 52 are connected to a cable 54 via a number of printed connections 53. The cable 54 links the probe 50 with the controller as in the previous embodiments. With this configuration, the probe 50 can be applied to a curved or flat surface thereby permitting relatively large areas to be assessed in a substantially shorter time than that would be required with a probe of the embodiments of FIGS. 2, 3 or 8.

Figure 10:
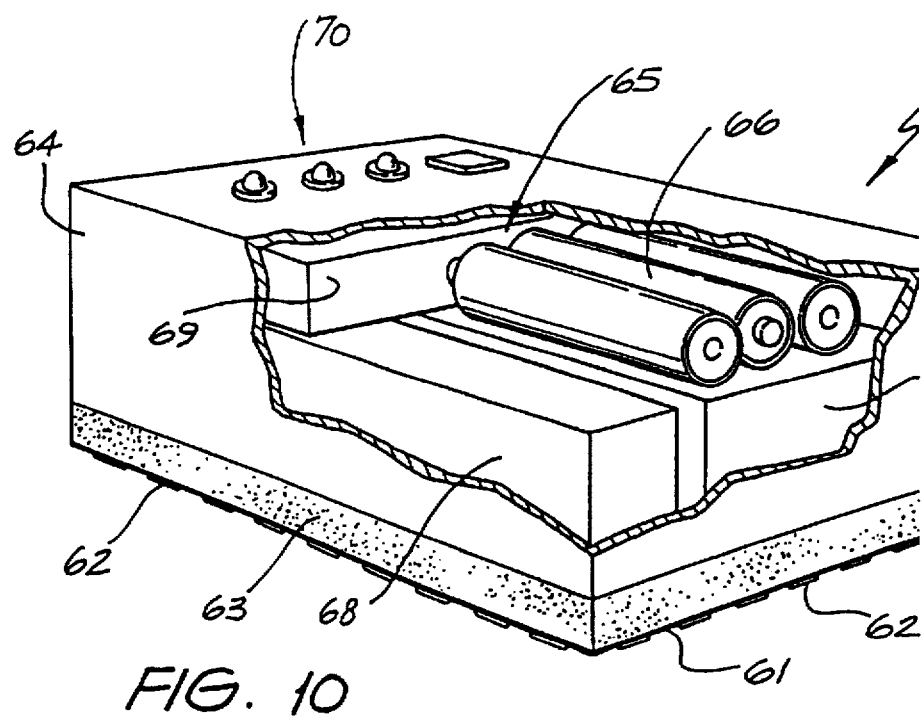

FIG. 10 illustrates an extension of the arrangement of FIG. 9 but of a totally integrated detector assembly 60. The detector assembly 60 incorporates a flexible substrate 61 arranged with a plurality of sensors 62 as in the probe 50. The substrate 61 is supported by an open cell foam support 63 which connects to a housing 64 within which a control unit 65 of the detector assembly 60 as formed. The support 63 permits flexing of the substrate 61 to match tissue contours whilst being supported from the control unit 65. The control unit 65 connects to the sensors 62 and incorporates, in a small hand held package, the processing functions required for external tissue type determination. The control unit 65 includes an integrated battery supply 66 together with a processor module 67, an input/output section 68 which connects to the sensors 62, and a control/display module 69. Connected to the control/display module 69 is a number of indicators 70 which provide either visual or audible feedback to the operator indicative of the tissue type when the probe assembly 60 is placed upon the surface of a living body.

Figure 11:
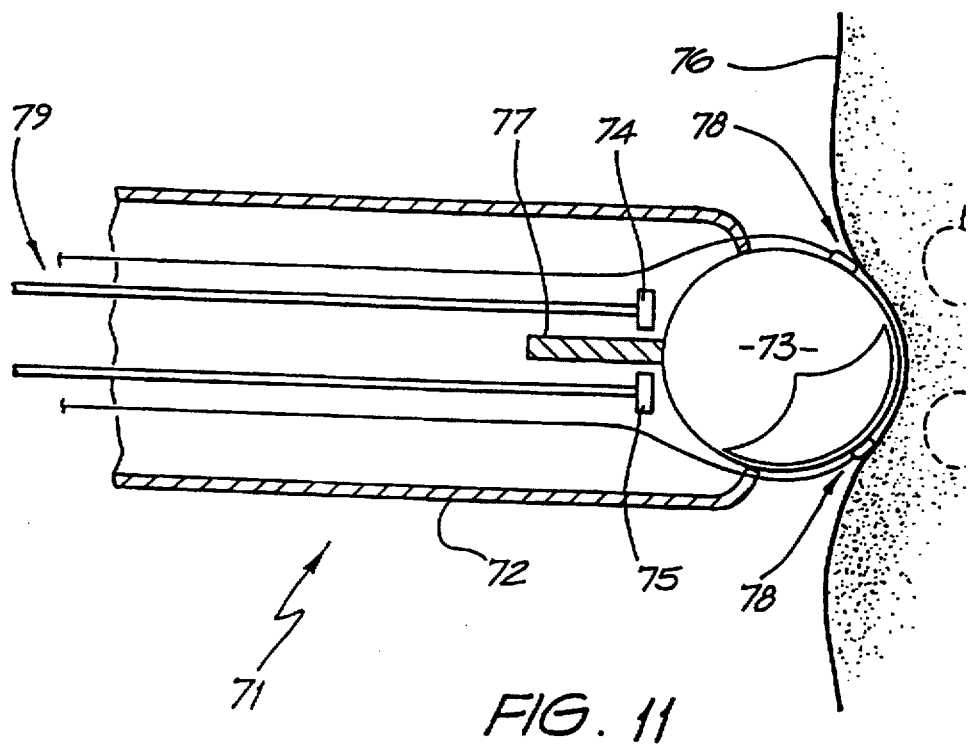
FIG. 11 is a side view of an optical sensor including a ball-refraction head.

FIG. 11 illustrates a ball refraction probe 71 which incorporates a shaft housing 72 and a clear (transparent) spherical refractive ball 73 arranged at the periphery of the shaft housing 72. Configured within the shaft housing 72 is a multiplicity of light sources 74 (only one of which is illustrated), such as light emitting diodes covering different spectral bands, and complementary light sensors 75 (again only one illustrated for clarity), such as light dependent resistors, PIN diodes, or other optical sensors. The probe 71 is configured so that the ball 73 acts to refract light emitted from each source 74 in a substantially spherical pattern to stimulate a large area of tissue 76 which is brought into contact with the ball 73. In a corresponding manner, backscattered light from the tissue 76 is refracted within the ball 73 and onto the sensor 75. An optically opaque barrier 80a prevents direct illumination from the sources 78 to the sensors 79. Two electrodes 78 are positioned on the ball 73 so as to contact the tissue 76 for electrical stimulation. A number of wire conductors 80 communicate signals between the probe 75 and the controller (not illustrated). As illustrated, a region 80 of the tissue 76 is illuminated by the sources 74, and a region 81 of the tissue is seen by the sensors 75, thus providing an indication of the light transmittance through the tissue 76 between the regions 80 and 81.

Figure 12:
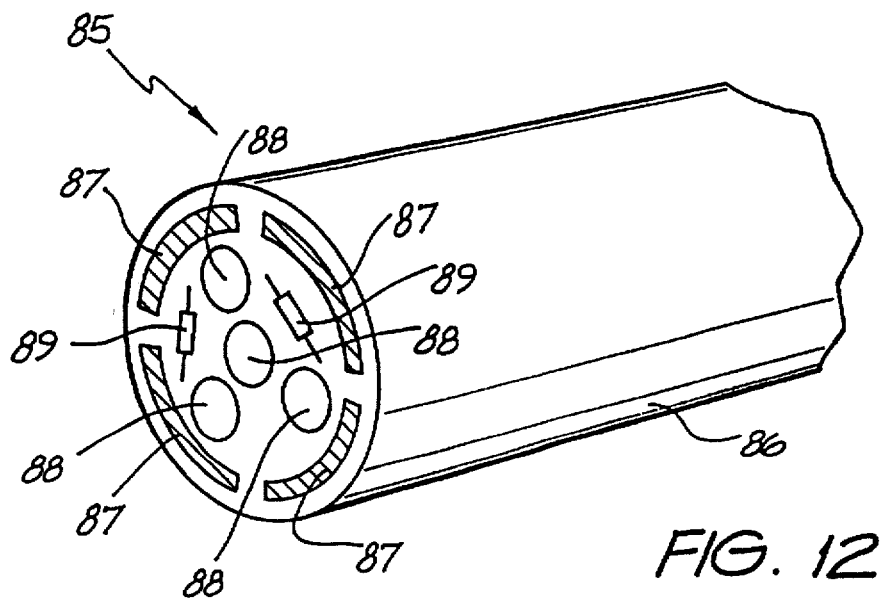
FIG. 12 is a view of another embodiment which includes ultrasonic transducers.

FIG. 12 shows an ultrasonic probe 85 which is formed upon a shaft 86 and which incorporates four electrical sensors 87 configured in a manner not unlike previously described embodiments. In particular, provided in the probe 85 are four ultrasonic transducers 88 each able to be energised separately in order to stimulate tissue brought into contact therewith. Where any one transducer 88 is stimulated, the remaining three can be used to receive the transmitted ultrasonic pattern. Received patterns can be processed to determine a variety of features relating to the density of the tissue and any changes in density throughout the tissue, which is indicative of blood flow. This can be performed using time of flight measurements such as use in known acoustic imaging systems such as in sonar and medical ultrasound. In order to compensate changes in acoustic coupling, a number of temperature sensors 89 are configured on the surface of the probe 85 which can be used to sense the temperature of tissue being sampled which can be used to compensate for changes in ultrasonic velocity therewithin.

Figure 13A:
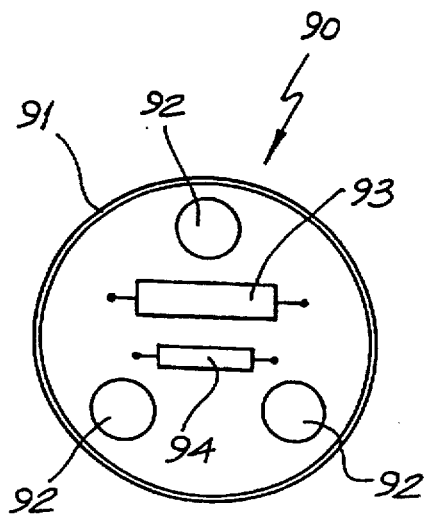
FIGS. 13A and 13B are end and side views respectively of a probe embodiment which incorporates thermal and optical stimuli.
Figure 13B:
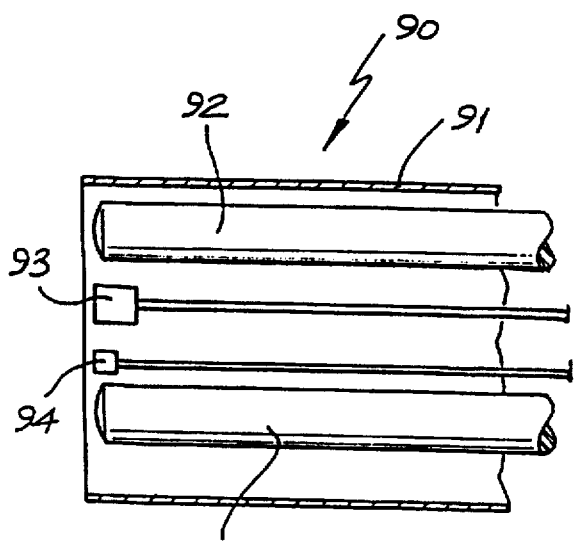

FIGS. 13A and 13B show a heat/light probe 90 which includes a tubular casing 91 along which are arranged three optical fibres 92. The fibres 92 are used to illuminate tissue being sampled and to receive transreflected light from the tissue. Also included in the probe 90 is a resistive heater 93 configured to selectively heat the tissue being probed, and a temperature sensor 94 configured to measure the temperature of the tissue in response to the action of the heater 93. In this manner, the thermal response time of the tissue type can be determined by the controller which provides an indication of blood flow through the tissue which can be indicative of pre-cancerous and cancerous cell growth.

Figure 14A:
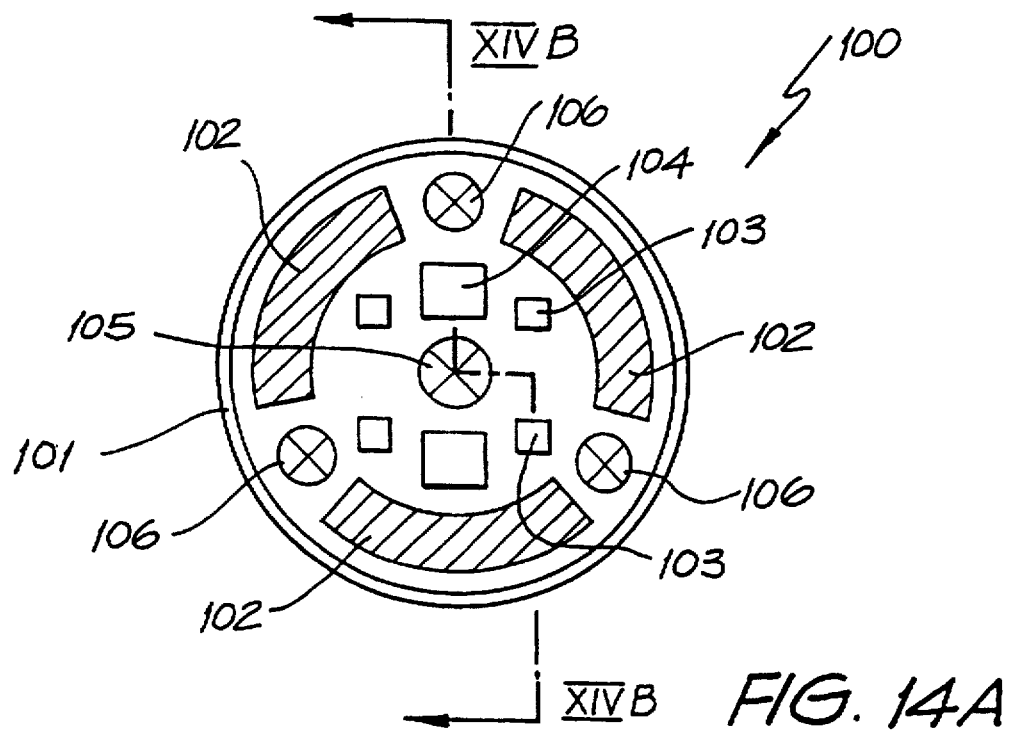
FIGS. 14A and 14B are end and side views respectively of a probe embodiment including electrical, optical and magnetic stimuli.
Figure 14B:
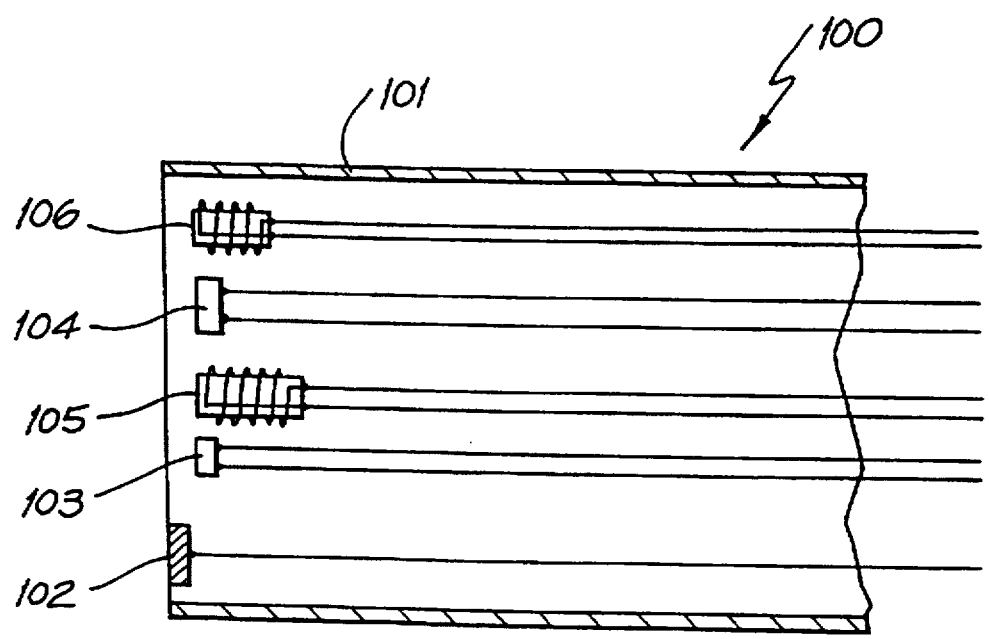

In FIGS. 14A and 14B, a magnetic probe 100 is shown which is, like previous embodiments, formed within a tubular casing 101. The probe 100 includes a number of electrodes 102 configured in a manner of previous embodiments. Also included are four optical transmitters 103 such as light emitting diodes arranged to transmit light at different wavelengths such as 1300 nm, 440 nm, 565 nm and 660 nm. Two optical receivers 104 are configured to receive light at different wavelengths, such as 1300 nm and 500–1000 nm. Also provided is a magnetic transmitter 105 centrally lodged within the probe 100 and three surrounding magnetic receivers 106. The magnetic transmitter 105 and receivers 106 incorporate a ferromagnetic core and a corresponding winding whereby the magnetic transmitter 105 establishes a small magnetic field extending from the end of the probe 100. Changes in the magnetic field are detected by the receivers 106 which can be compared whereby an imbalance between the signals received by each of the receivers 106 is indicative of a magnetic anomaly in the tissue.

Whilst at the time of writing this specification, the exact significance of magnetic stimuli is not known, it is believed that localised anomalies in the magnetic response of a tissue is due to a disturbance in the electrical charge that results from a function of the change of the partitioning within the cells of the tissue. Notably, surrounding the nucleus of a cell are a number of partitioning layers and it is believed that communication between those layers limits growth in normal cells. However, in cancerous cells, are only limited in communication between the layers appears to be limited which is believed to be directly related to the unconstrained growth of cancerous cells. Accordingly, an imbalanced distribution of electrical charge which can be detected or altered magnetically can be indicative of limited communication and therefore cancerous activity.

Preferably, a common control mechanism can be used for a number of different probe types and is therefore appropriate where the probes are interchangeable, the probes and/or the controller are able to be calibrated in a convenient manner such that reliable and consistent tissue sampling is achieved. The increased advent of microminiaturization increases feasibility for an ever larger plurality of the previously mentioned energy stimulate/receive forms within the tip of a single probe to enhance the number of discriminant parameters needed to detect cancer and pre-cancer.

In FIG. 15, a first calibration arrangement 120 is shown whereby a probe 122 connected to a controller 121 is contacted with a synthetic tissue substitute 123. The material 123 simulates well-defined known tissue properties in terms of backscattering and other energy emit/receive characteristics such as the electrical characteristics and in this manner, the controller 121 can be placed in an auto-nulling mode by which stimuli pulses output from the probe 122 and received signals can be verified as acceptable or adjusted such that they match within predetermined limits. Once suitably calibrated, the probe 122 can then be used and the synthetic substitute material 123 sterilised thereby preventing any a biological hazard.

FIG. 16 illustrates a second arrangement 125 which is pro-active as opposed to the embodiment of FIG. 15 being semi-active. In FIG. 16, the tip of a probe 126 is shown contacting a complimentary probe array 127 which forms part of a controller 128 to which the probe 126 is connected. In this manner, transmitters and receivers within each of the probe tip 126 and probe array 127 can be stimulated and because response of the probe array 127 is known, and consistent through an accurately calibrated drive arrangement 129, responses of the drive arrangement 129 can be detected by a calibration controller 130 which can then act to modify a drive arrangement 131 of the probe tip 126.

A third calibration arrangement 135 is shown in FIG. 17 where a probe 136, having an arrangement of conducting leads 137 from transducers (not illustrated) interconnect to a controller 141. Arranged within the probe 136 is a programmable read only memory (PROM) 138 which is programmed specific calibration values relating to the transducers in the probe 136. The PROM 138 connects directly to a calibration module 140 via a number of leads 139. The calibration module 140 outputs a number of gain control outputs 142 which supply an array of amplifiers 143 which are connected to the leads 137 to and from the transducers. In this manner, the gain of each of the amplifiers 143 is adjusted in response to the values within the PROM 138 so as to compensate for variations between the transducers on different probes 136. The PROM 138 network can also allow digital electronic standardization of the probe and keep track of each time that the probe is used in conjunction with the computer. The inclusion of the PROM 138 in the probe 136 permits the probe 136 to be electronically identifiable and each use of the probe 136 to be recorded thereby permitting, where appropriate, the number of repeated uses of the probe 136 being automatically restricted apriori.

Figure 18:
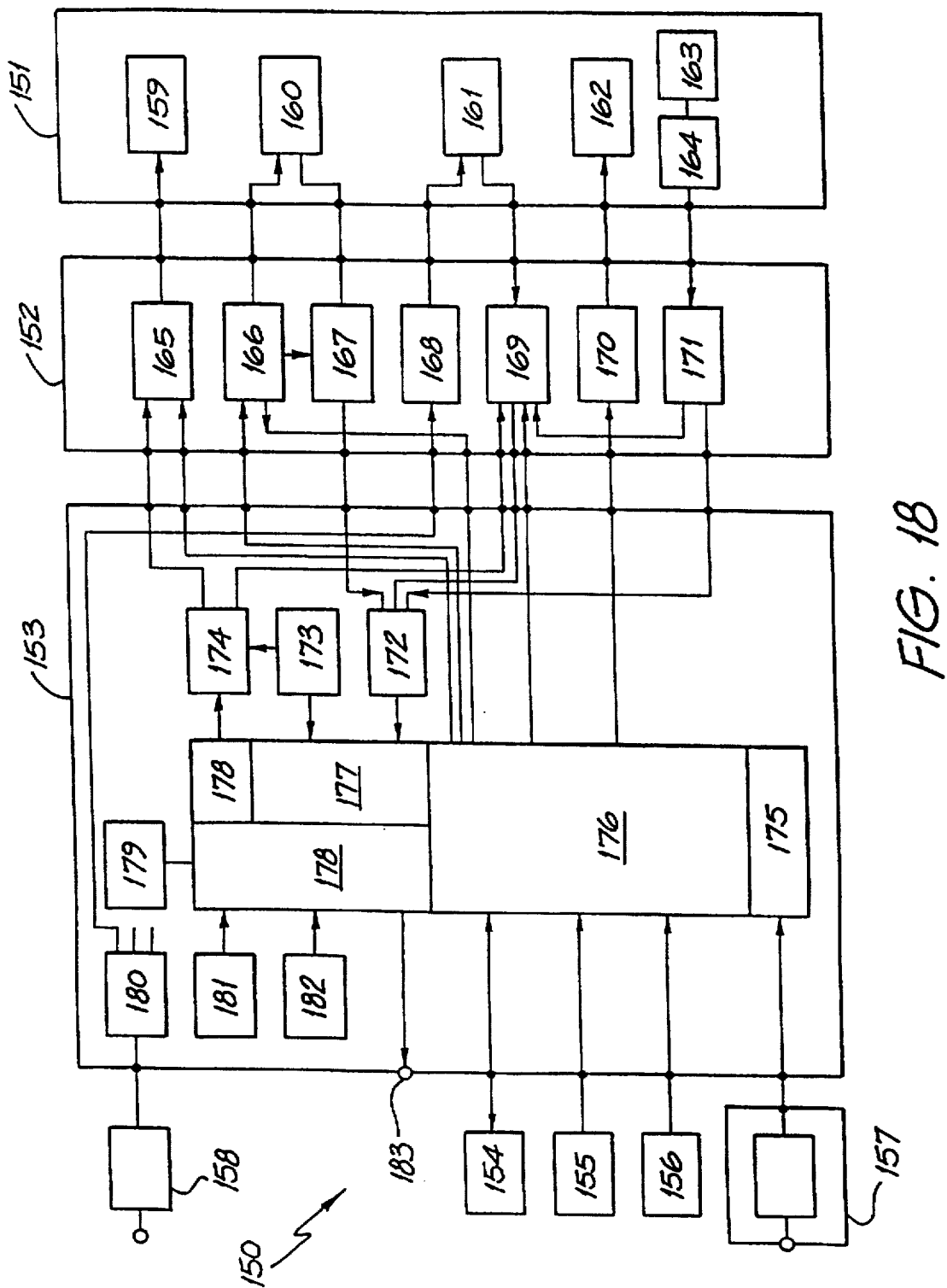
FIG. 18 is a schematic block diagram representation of a detection apparatus according to the preferred embodiment.

Turning now to FIG. 18, a preferred configuration of a detection system 150 is shown schematically which includes a probe 151 connected via an analog board 152 to a processor board 153. The processor board 153 outputs to a display 154 and includes user inputs obtainable through a number of control keys 155 and a numeric keypad 156. Computer type communications is available through an RS 232 style connection 157 or an IEEE 488 port or a COM# port or Direct Memory Access (DMA), with AC mains power being directly supplied via an input 158.

The probe 151 includes devices to provide a plurality of different physical stimuli. In particular, a number of light emitting diodes (LED's) 159 provide optical stimuli. Also, a number of electrodes 160 provide electrical stimuli to the tissue, which can be used for both determining discriminant values as well as for assessing the orientation of the probe 151 against the tissue. Additional components (not illustrated) for additive stimulate/receive discriminants can also be included in the manner previously described. To supplement the orientation of the probe 151, a number of strain gauges 161 provide an indication of the orientation of the probe 151, against the tissue. The probe 151 also includes a number of indicators 162 which can include either audible and/or optical indicators which provide feedback to the physician as to the type of tissue as it is assessed in real time. A number of photo diodes 163 provide electric optical sensing of light emitted from the LED's 159 and transreflected by the tissue. Because of the low signal intensity of output from the photo diodes 163, a pre-amplifier arrangement 164 is included in the probe 151. The probe 151 connects to the analog board 152 which includes drive and control amplifiers coupled to each of the elements of the probe 151.

The processor board 153 incorporates a microprocessor controller utilising a CPU 178a that is provided with a digital I/O block 176 as well as a serial I/O block 178b. The CPU 178a initiates stimuli which are output via a serial I/O block 178b to a digital to analog converter 174. The D/A converter outputs to a LED drive and control unit 165. LED drive and control unit 165 is used to supply the LED's 159 and is also input with digital signals via the digital I/O 176. Digital I/O 176 also outputs to an electrode drive unit 166 which coupled to the electrodes 160 for providing electrode stimuli pulses to the tissue. An amplifier 167 amplifies the outputs of the electrodes 160 which are routed through a protection unit 172 to an analog to digital converter 177 for assessment by the CPU 178a. Output of each photodiode preamplifier 164 is provided to an optical detector amplifier 171 whose output digitised using the A to D converter 177 for referencing by the CPU 178a. Alternative stimulate/receive energy transducers can also be included if required. A strain gauge drive 168 uses a DC signal from a DC power conditioning unit 180 and supplies the strain gauges 161 which output to a strain gauge amplifier 169. The amplifier 169 outputs via the protection unit 172 to the A to D converter 177 to measure the magnitudes of the forces being applied by the probe to the tissues. The digital I/O 176 also outputs to an indicator drive 170 which drives the indicators 162 in a known manner. The CPU 178a is supplied with a reset arrangement 181, a clock 182, and also outputs to a test socket 183.

As mentioned earlier, the probe 151 can be provided with a PROM (not illustrated) to permit calibration, ease of standardization, and record keeping of probe use. The PROM if used can connect directly to the digital I/O block 176.

In operation, a basic stimulation pattern is programmed or selected from a memory 179 by the CPU 178a and is used to stimulate the LED's 159 and electrodes 160. Raw data is recorded by the CPU 178a and stored in the memory 179 whereupon it is processed into a number of different discriminants. For each related series of samples taken, the multiple discriminants are then combined algorithmically to provide a tissue type categorisation. That categorisation is then compared with known categorisations stored within a non-volatile portion of the memory 179 and, where a match occurs, the categorisation is identified as being either normal tissue, pre-cancerous or cancerous and an indication provided to the physician as appropriate. Where the tissue type is unknown, a corresponding indication is provided to the physician which can prompt further examination of that particular part of the tissue.

When processing the raw sensed data, it is appropriate to select features that are relatively unrelated to normal patient-to-patient changes. This can include the processing of physical parameters such as electrical characteristics and optical characteristics both in the frequency and time domains so as to obtain frequency and time portrayals of electrical behaviour. Frequency components can be obtained by Fourier transformations or by measurements at different frequencies. Temporal responses relate to the amplitude of response relative to the energy imparted into the tissue. Swept frequency stimulation provides a spectral response resulting in a complex impedance consideration of the tissue type comprising nine or more separate parameters each with a corresponding spectral curve. Electrical temporal response can be determined by sequentially monitoring the observed response to a known electrical stimulus, typically a step function or impulse.

In optical arrangements the absolute backscattering of a sample can be determined as previously mentioned, along with the slope and rate of change of response, thereby providing as variables the first and second differential coefficients versus wavelength or time for spectral or temporal characterizations respectively.

For ultrasound transmissions density changes affect both the amplitude and Doppler effects and various combinations thereof which can be analysed by image analysis techniques. For magnetic stimuli, anomalies at particular frequencies or over a range of frequencies can be determined.

For each different type of tissue, various combinations of stimuli can be used. For example, for cervical cancer, the preferred types of stimuli are optical and electrical. For skin tissues, optical, electrical, magnetic, acoustic and thermal stimuli can be important.

Once the physical data and various discriminants are obtained, they can be combined to determine the particular type of tissue being examined. This can be done using discriminant analysis techniques, linear programming, cross correlations or neural networks. The preferred embodiment discriminant analysis techniques are used where expert opinions or empirically derived correlations are used to relate data so as to optimise the discriminant values. Essentially, various coefficients for each variable are assessed and a determination is made of what modifications are required to the variables in order for them to be mapped into a particular type of categorisation.

The preferred embodiment for detection of cervical cancer uses eight discriminants based on electrical and optical sensing. Those discriminants are backscattering of light at 540, 660, 940 and 1300 nm, and four shape features of the voltage decay curve.

The manner in which the discriminants are used to provide the tissue categorisation is algorithmic, and for cervical cancer and pre-cancer detection using the above identified discriminants, the combination is as follows:

$$P_i = A_i \cdot \sum_{j=1}^{n} (A_{ij} * VAR_j).$$

where $VAR_j$ is the real-time variable associated with position j in the linear equation, $A_{ij}$ is the constant coefficient for variable i, and $P_i$ is the relative probability of the i th tissue category.

In order to obtain accurate testing results, a large data base is required whereby known responses to particular types of cancers and pre-cancers can be correlated. For example, the present inventors, in the pursuit of embodiments relating to detecting cervical cancer, have examined over 2,000 subjects where each was analysed by an expert colposcopist and where relevant an histologist who provided reference data for significant tissue categories. Each of these subjects was also examined using a probe and system in accordance with the preferred embodiment, such that the responses of the preferred embodiment to the particular tissue types which have been manually categorised, can be cross referenced with the manual categorisation. This then forms the database for that particular type of cancer such that when the probe is applied to another patient the responses from that patient can, after processing through discriminant analysis, can be cross referenced to the database to identify the particular tissue type.

The present inventors have also performed similar experiments, and are developing databases in respect of breast cancer, skin cancer, colon cancer and prostate cancer. Each different type of cancer however presents different types of problems for the development of the database. In particular, for cervical cancer, in vivo examination can be performed however, for breast cancer, colon cancer and prostate cancer, biopsy results are necessary and therefore the database is developed about "in vitro" information. In skin cancers, dermatological examination as well as biopsy results can be used.

All samples are ratified by correlation of probe results against in vivo and biopsy identification which provides reference characteristics of each tissue type as they are detected by the probe.

Investigations by the present inventors regarding the performance of the preferred embodiment have indicated that detection system 150 (FIG. 18) for cervical cancer has provided between 85 and 99% concordance between colposcopy/histology and probe diagnosis depending on low grade abnormalities (well-developed human papilloma virus changes, minor atypia or cervical intraepithelial neoplasia grade 1), 90% on high grade abnormalities (cervical intraepithelial squamous neoplasia grade 2 or 3), to 99% on invasive cancer. Statistical analysis and extrapolation of these results suggest that the proportion of false positive and false negative rates using a probe arrangement of the preferred embodiment is of the order of 10% and therefore, in respect of cervical cancer, the present probe arrangement is a substantial improvement over the general 50–60% accuracy considered appropriate to the traditional pap smear test.

The foregoing describes only a number of embodiments of the present invention and modifications, obvious to those skilled in the art, can be made thereto without departing from the scope of the present invention.

What is claimed is:

1. An apparatus for categorization of a tissue type, comprising
   (1) a probe comprising a probe tip, said probe tip configured to contact a tissue surface area selected by contacting said area with said probe tip, said probe tip comprising
      a source of electrical current,
      a source of electromagnetic radiation,
      a sensor sensing from a tissue volume proximate said tissue surface a response to an electrical current from said current source, and
      a sensor sensing from said tissue volume proximate said tissue surface a response to electromagnetic radiation from said source of electromagnetic radiation,
      both of said sensors sensing responses from the same tissue volume before the probe is moved to contact another surface area, (2) a controller coupled to each of said sensors to receive each corresponding tissue response, said controller including a memory storing a known catalogue of expected tissue types and associated paired electrical current/electromagnetic radiation responses, and (3) a processor for processing paired responses from said tissue selected by contact with said probe tip and for analyzing said processed paired tissue responses, said processor processing the responses of said selected tissue to both of said sources to provide a categorization of the tissue type in accordance with a comparison of the tissue responses with said known catalogue of expected tissue types and associated paired responses.

2. The apparatus for categorization of a tissue type of claim 1, further comprising a calibration instrument comprising a synthetic tissue wherein said probe tip is contacted with said synthetic tissue, and said responses from said tissue are compared to predetermined limits.

3. The apparatus for categorization of a tissue type of claim 1, further comprising a calibration instrument having a complementary array in contact with said probe tip and comprising means to stimulate said probe sensors, wherein said responses from said tissue are compared to predetermined limits.

4. The apparatus for categorization of a tissue type of claim 1, wherein said probe comprises multiple arrays of electromagnetic and electric current sources and sensor elements configured to sample physical properties of selected tissue along the contour of a body organ.

5. The apparatus for categorization of a tissue type of claim 4, wherein said apparatus is configured to bring said probe tip in contact with a portion of a cervix.

6. The apparatus for categorization of a tissue type of claim 4, wherein said probe comprises flexible and conformable means to hold said sources and sensor elements along the contours of a body organ.

7. The apparatus for categorization of a tissue type of claim 4, wherein said probe tip has a distal end to contact said tissue surface area, said sensor sensing a response to said electrical current comprises at least three electrodes terminating at the distal end of said probe tip, said controller comprises circuitry to measure the potential differences between different pairs of said electrodes and to provide signals representative of said potential differences to said processor, and said processor comprises means to compare said measured potential differences between pairs of electrodes to determine that the probe is correctly oriented relative to said tissue surface, whereupon the processing of the paired responses of said selected tissue is enabled.

8. The apparatus for categorization of a tissue type of claim 7, further comprising means to signal an operator of said apparatus that the processing of paired responses has occurred.

9. The apparatus for categorization of a tissue type of claim 1, wherein said response to an electric current is a voltage decay after removal of an applied voltage to the tissue and said processor determines a value for the voltage decay.

10. The apparatus for categorization of a tissue type of claim 1, wherein said tissue type has a complex impedance in response to said source of electrical current and said processor determines a value for the complex impedance of the tissue over a range of frequencies.

11. The apparatus for categorization of a tissue type of claim 1, wherein said sensor sensing a response to an electrical current comprises electrodes, and said processor determines the current flow into the electrodes as a voltage is applied.

12. The apparatus for categorization of a tissue type of claim 11, wherein said apparatus comprises means to determine the current flow into one of the electrodes as a function of time.

13. The apparatus for categorization of a tissue type of claim 11, wherein said apparatus comprises means to determine the current flow into one of the electrodes as a function of frequency.

14. The apparatus for categorization of a tissue type of claim 1, wherein said sensor sensing a response to an electrical current comprises electrodes, and said processor determines a value for the current flow out of the tissue after the cessation of a voltage pulse applied to the electrodes.

15. The apparatus for categorization of a tissue type of claim 14, wherein said apparatus comprises means to determine the current flow into one of the electrodes as a function of time.

16. The apparatus for categorization of a tissue type of claim 14, wherein said apparatus comprises means to determine the current flow into one of the electrodes as a function of frequency.

17. The apparatus for categorization of a tissue type of claim 1, wherein said processor comprises means to determine a value for the conductivity of the selected tissue.

18. The apparatus for categorization of a tissue type of claim 17, wherein said sensor sensing a response to an electrical current comprises electrodes, said source of electric current comprises a sine wave voltage generator and said processor comprises means to determine from a value of the in-phase current flowing when said sine wave voltage generator applies a sine wave voltage to the electrodes.

19. The apparatus for categorization of a tissue type of claim 18, wherein said sine wave voltage generator comprises means to apply a sine wave voltage over a range of frequencies.

20. The apparatus for categorization of a tissue type of claim 1, wherein said sensor sensing a response to an electrical current comprises electrodes, and at least some of said electrodes are metal.

21. The apparatus for categorization of a tissue type of claim 20, wherein said probe tip has a face and said metal electrodes are formed from wires truncated at the probe tip face.

22. The apparatus for categorization of a tissue type of claim 20, wherein each of at least some of said electrodes has a shape chosen from the group consisting of circles, ellipses, squares, rectangles, triangles, segments of circles, and segments of annuli.

23. The apparatus for categorization of a tissue type of claim 20, wherein at least one electrode comprises an electrolytic cell coupled to the tissue by a salt bridge.

24. The apparatus for categorization of a tissue type of claim 20, wherein said metal electrodes are arranged symmetrically around the centroid of the probe tip.

25. The apparatus for categorization of a tissue type of claim 24, wherein said sensor sensing a response to electromagnetic radiation comprises a bundle of optical fibers and said apparatus further comprises an external tube having an internal surface, said metal electrodes comprise at least one electrode positioned in the center of said bundle of optical fibers and a plurality of cylindrical metal tube segments positioned adjacent and abutting against the internal surface of said external tube.

26. The apparatus for categorization of a tissue type of claim 20, wherein at least one of said electrodes is non-metallic.

27. The apparatus for categorization of a tissue type of claim 26, wherein said at least one non-metallic electrode is selected from the group consisting of a non-metallic semiconductor, silicon, carbon or titanium oxide bonded upon titanium.

28. An apparatus for categorization of a tissue type, comprising
   (1) a probe comprising a probe tip, said probe tip configured to contact at its distal end a tissue surface area selected by contacting said area with said probe tip, said probe tip comprising
      a source of electrical current,
      a sensor comprising at least three electrodes terminating at the distal end of said probe tip sensing from a tissue volume proximate said tissue surface a response to an electrical current from said current source,
   (2) a controller coupled to said sensor electrodes comprising circuitry to sequentially measure the potential difference between different pairs of said electrodes and to provide signals representative of said potential differences,
      said controller including a memory storing a known catalogue of expected tissue types and potential responses, and
   (3) a processor for processing responses from said tissue selected by contact with said probe tip and for analyzing said processed tissue responses, said processor processing the responses of said selected tissue to said source to provide a categorization of the tissue type in accordance with a comparison of the tissue responses with said known catalogue of expected tissue types and associated responses,
      said processor comprising means to compare said measured potential differences between pairs of electrodes for determining whether the probe is correctly oriented to said tissue surface.

29. An apparatus for categorization of a tissue type, comprising
   (1) a probe comprising a probe tip, said probe tip configured to contact a tissue surface area selected by contacting said area with said probe tip, said probe tip comprising
      a source of a first energy type,
      a source of a second energy type,
      a sensor sensing from a tissue volume proximate said tissue surface a response to energy from said source of a first energy type, and
      a sensor sensing from said tissue volume proximate said tissue surface a response to energy from said source of a second energy type,
      both of said sensors sensing responses from the same tissue volume before the probe is moved to contact another surface area,
   (2) a controller coupled to each of said sensors to receive each corresponding tissue response, said controller including a memory storing a known catalogue of expected tissue types and associated paired first energy type/second energy type responses, and
   (3) a processor for processing paired responses from said tissue selected by contact with said probe tip and for analyzing said processed paired tissue responses, said processor processing the paired responses of said selected tissue to both of said sources to provide a categorization of the tissue type in accordance with a comparison of the paired tissue responses with said known catalogue of expected tissue types and associated paired responses.

30. The apparatus for categorization of a tissue type of claim 29, further comprising a calibration instrument comprising a synthetic tissue wherein said probe tip is contacted with said synthetic tissue, and said apparatus response is compared to predetermined limits.

31. The apparatus for categorization of a tissue type of claim 29, further comprising a calibration instrument having a complementary array in contact with said probe tip and comprising means to stimulate probe sensors, wherein said apparatus response is compared to predetermined limits.

32. The apparatus for categorization of a tissue type of claim 29, wherein said probe comprises multiple arrays of electromagnetic and electric current sources and sensor elements configured to sample physical properties of selected tissue along the contour of a body organ.

33. The apparatus for categorization of a tissue type of claim 32, wherein said apparatus is configured to bring said probe tip in contact with a portion of a cervix.

34. The apparatus for categorization of a tissue type of claim 32, wherein said probe comprises flexible and conformable means to hold said sources and sensor elements along the contours of a body organ.

35. The apparatus for categorization of a tissue type of claim 29, wherein
   said probe tip has a distal end to contact said tissue surface area,
   said sensor sensing a response to said first or second energy types comprises at least three sensor elements receiving signals from the distal end of said probe tip,
   said controller comprises circuitry to measure the differences in response between different pairs of said sensor elements and to provide signals representative of said differences in response to said processor, and
   said processor comprises means to compare said measured differences in response between pairs of sensor elements to determine that the probe is correctly oriented relative to said tissue surface, whereupon the processing of the paired responses of said selected tissue is enabled.

36. The apparatus for categorization of a tissue type of claim 35, further comprising means to signal an operator of said apparatus that the processing of paired responses has occurred.

37. An apparatus for categorization of a tissue type, comprising
   (1) a probe comprising a probe tip, said probe tip configured to contact at its distal end a tissue surface area selected by contacting said area with said probe tip, said probe tip comprising
      a source of a first energy type,
      a sensor comprising at least three first sensor elements terminating at the distal end of said probe tip sensing from a tissue volume proximate said tissue surface a response to first energy type from said source of a first energy type,
   (2) a controller coupled to said sensor elements comprising circuitry to sequentially measure the difference in response between different pairs of said sensor elements and to provide signals representative of said differences,
      said controller including a memory storing a known catalogue of expected tissue types and potential responses, and (3) a processor for processing responses from said tissue selected by contact with said probe tip and for analyzing said processed tissue responses, said processor processing the responses of said selected tissue to said source to provide a categorization of the tissue type in accordance with a comparison of the tissue responses with said known catalogue of expected tissue types and associated responses, said processor comprising means to compare said measured differences in response between pairs of sensor elements for determining whether the probe is correctly oriented to said tissue surface.

38. The apparatus for categorization of a tissue type of claim 37, further comprising a source of a second energy type and a sensor comprising second sensor elements terminating at the distal end of said probe tip sensing from a said tissue volume proximate said tissue surface a response to a second energy type from said source of a second energy type.

39. The apparatus of one of claims 29–38 wherein said first energy type is ultrasonic energy.

* * * * *